United States Patent [19]

della Valle et al.

[11] Patent Number: 4,713,374
[45] Date of Patent: Dec. 15, 1987

[54] GANGLIOSIDE DERIVATIVES

[75] Inventors: Francesco della Valle, Padua; Aurelio Romeo, Rome, both of Italy

[73] Assignee: Fidia, S.p.A., Abano Terme, Italy

[21] Appl. No.: 749,092

[22] Filed: Jun. 26, 1985

[30] Foreign Application Priority Data

Jun. 27, 1984 [IT] Italy .............................. 48492 A/84

[51] Int. Cl.$^4$ ....................... C08G 18/08; C08G 18/18
[52] U.S. Cl. ........................................ 514/54; 536/53; 536/55.1
[58] Field of Search ................... 536/53, 55.1; 514/54

[56] References Cited

U.S. PATENT DOCUMENTS

| 4,415,733 | 11/1983 | Tayot | 536/55.1 |
| 4,435,389 | 3/1984 | Mutai et al. | 514/54 |
| 4,437,244 | 8/1982 | Mynard et al. | 424/180 |
| 4,469,795 | 9/1984 | Ginns et al. | 436/504 |
| 4,476,119 | 10/1984 | Valle et al. | 514/25 |
| 4,521,593 | 6/1985 | Martin | 536/53 |

FOREIGN PATENT DOCUMENTS 0072722  2/1983  European Pat. Off. .......... 536/17.9

OTHER PUBLICATIONS

McCluer et al., Adv. Exp. Med. Biol., 19, 95–102 (1979).
Saito et al., J. Lipid Res., 12, 257–259 (1971).
MacDonald et al., J. Lipid Res., 21, 642–645 (1980).
Young et al., Meth. Enzym., 50, 137–141 (1979).

Primary Examiner—Ronald W. Griffin
Attorney, Agent, or Firm—Birch, Stewart, Kolasch & Birch

[57] ABSTRACT

New functional ganglioside derivatives comprising ester, amide and peracylated derivatives of gangliosides, preparation procedures therefor, pharmaceutical preparations containing the same, and the therapeutic use of the derivatives.

39 Claims, No Drawings

GANGLIOSIDE DERIVATIVES

BACKGROUND AND FIELD OF THE INVENTION

The present invention relates to new functional ganglioside derivatives and more precisely to new esters and amides, their preparation procedures, pharmaceutical preparations containing the ganglioside esters and amides and to the therapeutic use of the ganglioside esters and amides.

Gangliosides are natural products contained in various animal tissues or organs, above all in the tissues of the central and peripheral nervous systems, but also in the adrenal marrow, in the erythrocytes, in the spleen and elsewhere, from which they can be extracted in a purified form. It has been possible to establish the basic structure of most gangliosides thus obtained. They are glycosphingolipids, that is, compounds resulting from the union of an oligosaccharide with a sphingosine and a certain number of sialic acids bound together by glucosidic or ketosidic bonds. The gangliosides so far described in the literature and obtained in purified form do not represent unitary chemical compounds, except possibly for their saccharide part (oligosaccharide), as the ceramide and sialic components are quite variable, within certain limits. Thus, even when "pure" gangliosides are referred to, this expression is to be broadly interpreted to mean a ganglioside species in which at least a part, for instance the saccharide part, is unitary and characteristic from a chemical point of view. Given this, before describing in more detail the background of the present invention, it is useful to take note of the following general formula which includes all the structures of the gangliosides so far obtained in purified form, and emphasizes the functions which are functionally modified according to the invention (formula I).

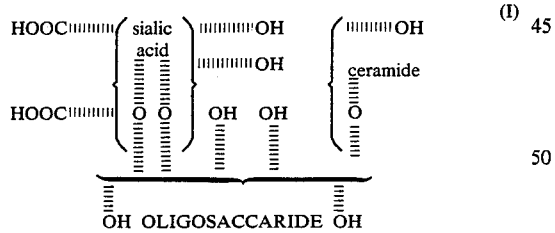

In this formula, an oligosaccharide residue, formed by a maximum of 5 monosaccharides, is connected by a glucoside bond to a ceramide residue and to one or more sialic acid residues, both by means of as many direct glucoside bonds, and by means of one or more such bonds, as the remaining sialic acid residues are joined together by ketoside bonds. The formula shows the hydroxyl groups of the saccharide portion, of the sialic acids and of the ceramide, as well as the above mentioned glucoside bonds with sialic acids and ceramide and the carboxyl groups of the sialic acids. The sialic acids which form part of the gangliosides of formula I have the general structure II

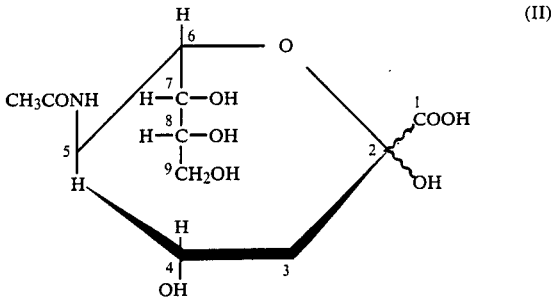

in which one or more of the primary and secondary hydroxyl groups may also be acylated and in which the acyl groups derive from acetic or glycolic acid. The number of sialic acids present in gangliosides usually varies from 1 to 5.

The sialic residues are bound to the oligosaccharide by a ketosidic bond formed by the hydroxyl in position 2 with an oligosaccharide hydroxyl. When several sialic acids are bound together, their molecules are united by means of ketoside bonds formed among the hydroxyls of positions 2 and 8 of two sialic acid molecules. The sialic acids of gangliosides, including purified gangliosides as described above, are mixtures of various chemically unitary acids, such as N-acetylneuraminic and N-glycolylneuraminic acids, in which the first is predominant, and possibly of one or more of their O-acyl-derivatives, such as 8-O-acylderivatives.

Gangliosides are to be found in nature as metallic salts, such as sodium salts, and it is therefore the carboxylic function/s of sialic acids which are salified. The free forms of gangliosides may be easily obtained by treatment of the salts, such as sodium salts, which an acid type ionic exchanger, using for example a resin such as Dowex AG 50×8, H+ form.

The ceramide residue in the gangliosides of formula I generally represents several N-acyl sphingosine having one of the formulas

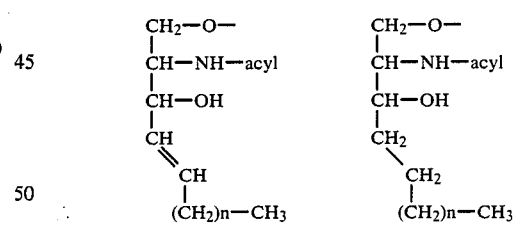

in which n=10–16 and the acyl derives from a saturated or unsaturated fatty acid having between 16 and 22 carbon atoms, or from a corresponding hydroxyacid.

The oligosaccharide is made up of a maximum of 5 monosaccharides or their derivatives with an acylaminic group, especially of hexoses and their derivatives of the above mentioned type. At least one glucose or galactose molecule is, however, always present in the oligosaccharide. The most frequent residue present as an acylaminic derivative of the above mentioned sugars is N-acetylgalactosamine or N-acetylglucosamine.

In order to better illustrate the structure of the gangliosides included in formula I and in particular the character of the bonds between the saccharide parts, the sialic acids and ceramide, reproduced below is the formula of a "pure" GM$_1$ ganglioside containing only one sialic acid (represented by N-acetylaminic or N-glycolylneuraminic acid).

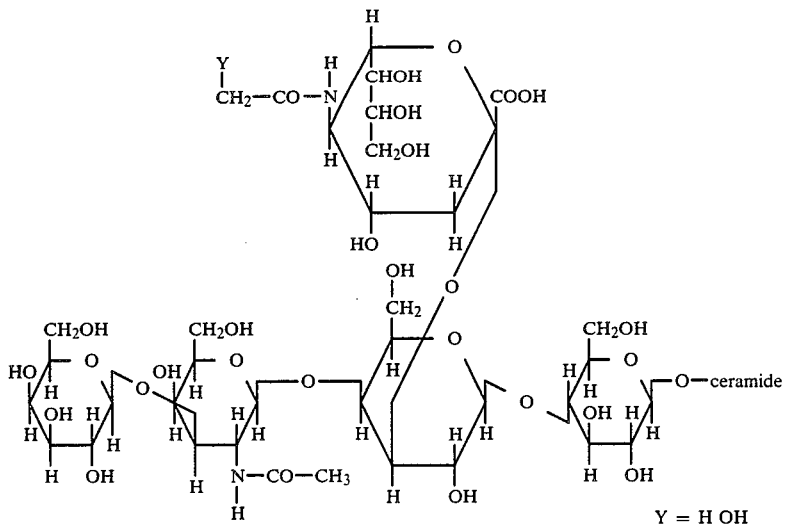

It is well known that gangliosides are functionally important in the nervous system and it has recently been shown that gangliosides are useful in the therapy of peripheral nervous system pathologies. The therapeutic action of gangliosides seems to consist above all in stimulating sprouting phenomena of the nervous cell and in activating the membrane enzymes involved in the conduction of nervous stimuli, such as the enzyme (Na+, K+) ATPase. Neuronal sprouting stimulated by gangliosides promotes functional recovery of the damaged nervous tissue.

Further studies have been carried out to find compounds which could prove more efficient than gangliosides in the therapy of nervous system pathologies. These studies have led for example to the discovery that internal esters of gangliosides, in which one or more hydroxyls of the saccharide part are esterified with one or more carboxylic groups of the sialic acids (intramolecular reaction) with the formation of as many lactonic rings, are more active than gangliosides themselves in promoting neuronal sprouting and in activating membrane enzymes involved in the conduction of nervous stimuli, such as the enzyme Na+, K+) ATPase (see U.S. Pat. No. 4,476,119).

According to the present invention, another group of ganglioside derivatives has now been discovered, which presents advantages over gangliosides themselves, inasmuch as they have a prolonged activity in time ("retard" effect). These compounds are derivatives in which the carboxyl group of the sialic acids are functionally modified by esterification or by conversion into amides and derivatives of those esters or amides in which the hydroxyl groups of the saccharide part, of the sialic acids and of the ceramide are also esterified with organic acids, or rather acylate derivatives (which shall be simply called "acylates" hereinafter, and specifically "acetylates, propionylates, etc."). The derivatives of the invention also include ganglioside derivatives in which only the hydroxyl groups are esterified with organic acids, that is, contain free carboxyl groups.

Two methyl esters of the carboxyl of a sialic acid of gangliosides were described in the article "Notes on improved procedures for the chemical modification and degradation of glycosphyngolipids" in the Journal of Lipid Research 21, 642–645 (1980) by MacDonald et al. These compounds are the methyl esters of the ganglio-sides $G_{M1}$ and $G_{M3}$ [(the abbreviations used herein to identify gangliosides are those proposed by Svennerholm in J. Jeurochem. 10, 613 (1963))]. However, MacDonald et al. do not report any biological activity for the compounds. The methyl ester of the ganglioside $G_{M3}$ is also used in the preparation of one of its peracylate derivatives for use in several degradation or copulation reactions [Methods of Enzymology, 50, 137–140 (1978)]. The above mentioned article in Journal of Lipid Research by MacDonald et al. also describes an acetylation of the methyl esters of gangliosides $G_{M1}$ and $G_{M3}$, but without isolating the acylated compounds.

Acetylation with acetic anhydride-pyridine of lipids extracted from the spleen, liver and kidneys of Buffalo rats, from Morris hepatomas and from fibroblast cells was described by Terunobo Saito and Sen-Itiroh Hakomori in the Journal of Lipid Research, 12, 257–259, (1971). The authors isolated by chromatography the acetylated mixture of the gangliosides contained in those lipids from the acylated product, together with other glycolipids without, however, identifying any specific ganglioside. Of the amides, the unsubstituted amide of the ganglioside $G_{M3}$ was described [Ad. Exp. Med. Biol. 19, 95 (1972)], but even in this case, no biological properties were mentioned.

OBJECTS AND SUMMARY OF THE INVENTION

One of the first objects of the present invention, therefore, resides in providing the new functional ganglioside derivatives discussed above, that is, the esters and amides of the carboxyl groups of gangliosides defined in formula I, or of their mixtures, the peracylated derivatives of these esters and amides in the hydroxyl groups of the oligosaccharide, of sialic acids and ceramide of gangliosides of formula I or of their mixtures with free carboxylic functions, and salts thereof.

A second object of the invention resides in providing new pharmaceutical preparations containing both the new functional derivatives defined above together with the well known ones described above.

A third object resides in the therapeutic use of all these ganglioside derivatives.

DETAILED DESCRIPTION OF THE INVENTION

A. The ganglioside starting compounds

The present invention comprises new useful ganglioside derivatives. These new derivatives are particularly derived by functionally modifying the carboxyl and/or hydroxyl groups present in the basic ganglioside structure. Gangliosides thus far obtained in purified form can be represented by the following formula (I) which also emphasizes the functional groups modified according to the present invention:

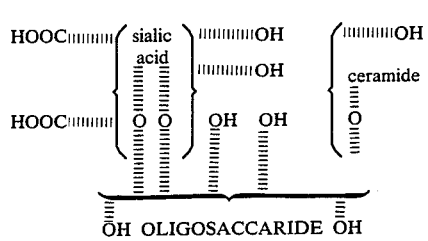

These gangliosides which form the starting materials for the functional derivatives of the invention are all those which may be extracted from various animal organs and tissues, especially from the tissues of the central and peripheral nervous systems, for example from the brain, cerebrospinal fluid, muscles, plasma and blood serum, kidneys, adrenals, liver, spleen, intestine, and erythrocytes or leukocytes. The starting gangliosides may also be the purified ones described in literature, such as those extracted from tissues and organs of vertebrates, especially mammals such as man, cattle, calf, rat, mouse or from microorganisms.

According to the present invention, these ganglioside compounds are modified by functionallly modifying the hyroxyl and/or carboxyl groups in the starting ganglioside molecule to produce new ganglioside derivatives. The new derivatives of the invention are particularly obtained by (a) subjecting the carboxyl groups to esterification or conversion to an amide; and/or (b) acylating the hydroxyl groups present in the ganglioside.

The esters or amides which are the new derivatives of the invention are particularly monoesters and monoamides in the case of monosialogangliosides and polyesters and polyamides in the case of polysialogangliosides, with as many ester or amide groups as there are carboxyl groups present in the molecule and, therefore, as many sialic acid groups as are present.

Ganglioside derivatives according to the invention can be prepared by modifying "purified" individually characterized gangliosides or by modifying a mixture of gangliosides, such as a mixture of monosialogangliosides and polysialogangliosides. In the mixtures which are used for esterification or conversion into amides for the preparation of active compounds according to the invention, such as for example the mixture described in Example 3 hereinbelow, containing both monosialogangliosides and polysialogangliosides, all of the carboxyl groups are modified and derivatives are obtained which are totally esterified or converted into amides. The description "esters or amides" utilized herein in this description should therefore be interpreted in this sense to mean totally esterified or converted into amides. This also applies especially for the derivatives of the illustrative Examples given below which are simply referred to as "esters or amides". These statements mean mixtures containing polysialogangliosides which are totally esterified or converted in the amides in all of the carboxyl groups.

Thus, the present invention encompasses derivatives of gangliosides whether derived from a single "purified" ganglioside or from a mixture of gangliosides. The invention further encompasses derivatives obtained from various ganglioside structures, particularly as the structure of the ganglioside may vary with respect to the number and kind of sialic acid residue, ceramide residue, or oligosaccharide residue.

Regarding their structure, the basic starting gangliosides may be monosialo-, disialo-, trisialo-, tetrasialo-, or pentasialogangliosides, with the preferred sialic acids being N-acetylneuraminic and N-glycolylneuraminic acids. The sialic acids may also be acylated at one of the hydroxyls of their lateral chain, such as the hydroxyl in position 8, if this position is not already occupied by a ketosidic bond which binds it to another adjacent sialic residue.

The ceramide part may vary, in the manner discussed above, and also in the length of the carbon atom chains of the sphingosines which comprise a part of the ceramide which may vary from 16 to 22 carbon atoms. In addition, the length of any acyl residue may also vary, particularly within the same limits of 16 to 22 carbon atoms. Apart from this, the ceramide residue may vary in that the double sphingosine bond may be absent or present and usually this residue is largely composed of unsaturated N-acylated sphingosine and of a low percentage of the corresponding saturated compound (which may however reach about 10%). The acyl group may also be derived from aliphatic hydroxyacids with the above mentioned number of carbon atoms varying from 16 to 22. One particularly important group of gangliosides contains, in the ceramide residue, acylated sphingosines with 18 or 20 carbon atoms in their chains and corresponding saturated compounds, while their saturated or unsaturated acyl group, unsubstituted by hydroxyls, has the same number of 18 or 20 carbon atoms.

As discussed above, the present invention relates, on the one hand, to functional derivatives of "pure" gangliosides of formula I, that is with a unitary composition as described above, and, on the other hand, to the functional derivatives of ganglioside mixtures, for example, in the extract form as they are obtained from various animal tissues. In the first case the basic gangliosides are preferably those in which the oligosaccharide is formed by a maximum of 4 hexose residues or N-acetylhexosamine, since at least one hexose residue is present, and in which this saccharide part is chemically unitary. The hexoses are preferably chosen from the group consisting of glucose and galactose and the N-acetylhexosamines from the group comprising N-acetylglucosamine and N-acetylgalactosamine (ganglioside group A). The gangliosides in this group are, for example, those extracted from the brains of vertebrates, such as those described in the article "Gangliosides of the Nervous System" in Glycolipid Methodology, Lloyd A. Witting Fd., American Oil Chemists' Society, Champaign, Ill. 187–214 (1976) see especially plate 1), for example gangliosides $G_{M4}$, $G_{M3}$, $G_{M2}$, $G_{M1}$-GlcNAc, $G_{D2}$, $G_{D1a}$-GalNAc, $G_{T1c}$, $G_Q$, $G_{T1}$ and especially those in which the oligosaccharide contains at least one glucose or galactose residue and one N-acetylglucosamine or N- acetylgalactosamine residue, especially the following (ganglioside group B)

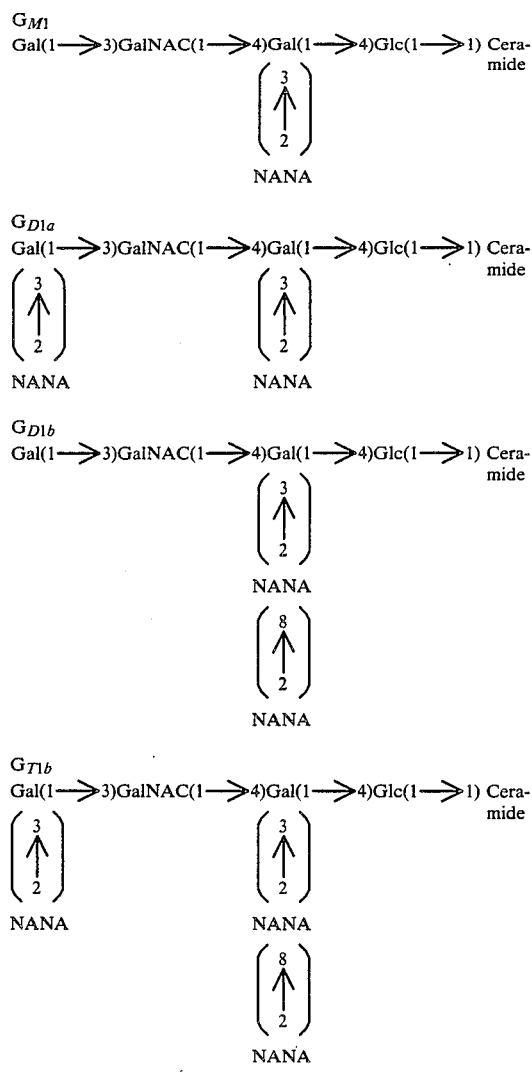

where Glc stands for glucose, GalNAc stands for N-acetylgalactosamine, Gal stands for galactose, and NANA stands for N-acetylneuraminic acid.

If ganglioside mixtures are used as the starting material for functional conversions according to the present invention, the mixtures may consist of those directly obtained by extraction of gangliosides from various animal tissues as "total" ganglioside extracts or as various fractions thereof. Such extracts are described in literature for example, in the articles mentioned above or also in "Extraction and analysis of materials containing lipidbound sialic acids" in Glycolipid Methodology, Lloyd A. Witting Fd., American Oil Chemists' Society, Champaign, Ill. 159-186 (1976) and "Gangliosides of the Nervous System" from the same book, pp. 187-214. Some of the most important mixtures to be used according to the present invention are ganglioside extracts obtained from tissues from the nervous system, in particular from the brain, and containing gangliosides $G_{M1}$, $G_{D1a}$, $G_{D1b}$ and $G_{T1b}$ already mentioned above. Mixtures of this type are for example those described in Example 2.

B. Types of ganglioside derivatives of the invention

Specified hereinafter are the specific alcohol, amide and acyl functions which are especially suitable for obtaining particularly interesting new compounds according to the invention and these functional groups are to be taken into consideration both for "pure" unitary gangliosides and for mixtures, especially those listed here.

In each of the ganglioside groups mentioned above the carboxyl groups of the sialic residues are present according to one of the objects of the present invention in esterified form, or in the form of amides.

1. Esterification

The groups of esters in the new ganglioside derivatives derive in particular from alcohols of the aliphatic series and especially from those with a maximum of 12 and especially 6 carbon atoms, or from those of the araliphatic series with preferably only one benzene ring, possibly substituted by 1-3 lower alkyl groups ($C_{1-4}$), for instance methyl groups, and a maximum of 4 carbon atoms in the aliphatic chain, or alcohols of the alicyclic or aliphaticalicyclic series with only one cycloaliphatic ring and a maximum of 14 carbon atoms or of the heterocyclic series with a maximum of 12 and especially 6 carbon atoms and only one heterocyclic ring containing an atom are chosen from the group formed by N, O and S. The amide groups of the carboxylic functions in the ganglioside derivatives of the present invention derive from ammonia or amines of any class having preferably a maximum of 12 carbon atoms.

The alcohols and amines mentioned above may be substituted or unsubstituted, especially by functions chosen from the group formed by hydroxyl, amine, alkoxyl groups with a maximum of 4 carbon atoms in the alkyl, carboxyl or carbylcoxy (such as carbonylmethoxy and carbonylethoxy) groups with a maximum of 4 atoms in the alkyl, alkylamine or dialkylamino residue with a maximum of 4 carbon atoms in the alkyls, and may be saturated or unsaturated, especially with only one double bond. The alcohols esterifying the carboxylic functions of gangliosides according to the present invention may be monovalent or polyvalent, especially bivalent. Of the alcohols of the aliphatic series, those lower alcohols with a maximum of 6 carbon atoms are preferred, such as methyl alcohol, ethyl alcohol, propyl and isopropyl alcohol, normal butyl alcohol, isobutyl alcohol, tertiary butyl alcohol, and of the bivalent alcohols, ethyleneglycol and propyleneglycol. Of the alcohols in the araliphatic series, those with only one benzene residue are preferred, such as benzyl alcohol and phenethyl alcohol; of the alcohols of the alicyclic series, preferred are those with only one cycloaliphatic ring, such as cyclohexyl alcohol (cyclohexanol), or terpene alcohols, such as menthanol, carvomenthol, or one of the terpineols or terpinenols or piperitols. Of the alcohols in the heterocyclic series, tetrahydrofuranol or tetrahydropyranol are preferred. For the esterification of the carboxylic ganglioside groups, substituted aliphatic alcohols may also be used, for example, with amine functions, like aminoalcohols, such as those with a maximum of 4 carbon atoms and especially aminoalcohols with dialkyl($C_{1-4}$)-amine groups such as diethylaminoethanol.

2. Preparation of amides

The carboxylic functions converted to an amide group according to the present invention either derive from ammonia (and the amide is in this case the unsubstituted amide —$CONH_2$) or from primary or secondary amines, especially from those containing a maximum of 12 carbon atoms. These amines may be of an aromatic, heterocyclic or alicyclic, nature, but are especially aliphatic. The major object of the present invention is the carboxylic derivatives of aliphatic amines with a maximum of 12 carbon atoms, and these amines may have open, straight or ramified chains or may be cyclic, such as the alkylamines derived from alkyls with between 1 and 6 carbon atoms, such as methylamine, ethylamine, ethylmethylamine, propylamine, butyl amine hexylamine, dimethylamine, diethylamine, diisopropylamine, dihexylamine, or benzylamine.

These amine groups may further be substituted by groups chosen from the group formed of aminic, alkylaminic or dialkylaminic groups with a maximum of 4 carbon atoms in the alkyl groups, or by hydroxyl or alkoxyl groups with a maximum of 4 carbon atoms in the alkyl groups, such as dimethylaminoethylamine, dimethylaminopropyl-1-amine and 6-hydroxyhexyl-1-amine, or alkylenamines derived from alkylene groups with straight chains with between 3 and 6 carbon atoms or corresponding chains substituted by 1 to 3 methyl groups, such as pyrrolidine, piperidine and azepine. The alkyl or alkylene groups of these amines may also be interupted in the carbon atom chain or substituted by other heteroatoms, in particular by nitrogen atoms, and the amides of the invention are derived in this case from diamines, such as ethylenediamine, trimethylendiamine, piperazine; or should the alkyl or alkylene groups be interrupted or substituted by oxygen or sulphur atoms the amides represent aminoalcohol derivatives, such as aminoethanol or aminopropanol or are derivatives of morpholine or thiomorpholine. These groups thus include e.g. alkylamines of the above said type, e.g. alkylamines and dialkylamines of the above type, e.g. of 1–6 carbon atoms, which are further substituted in the alkyl moieties by further aminic, alkylamino or dialkylamino groups with a maximum of 4 carbon atoms in the alkyl groups, or by hydroxyl or alkoxyl groups with a maximum of 4 carbon atoms in the alkyl groups, such as dimethylaminoethylamino, 3-dimethylamino-propyl-1-amino and 6-hydroxy-hexyl-1 amino groups. The esters and amides specified above of the gangliosides of groups A and B previously mentioned, and of their mixtures, are of special interest in the present invention.

3. Acylation

The invention also includes the peracylated derivatives in the hydroxyls of the saccharide part, of the sialic acids and ceramide of the esters and of the amides described here. In these derivatives the acyl groups may be derived from acids of the aliphatic, aromatic, araliphatic, alicyclic or heterocyclic series; preferably from acids of the aliphatic, aromatic, araliphatic, alicyclic or heterocyclic series with a maximum of 10 carbon atoms and especially 6 atoms, such as formic, acetic, propionic acid, the butyric and valerianic acids and capronic or caprinic acid. They may also be derived from acids for example with the same number of carbon atoms, but substituted particularly by hydroxyacids, such as lactic acid, aminoacids, such as glycine, or bibasic acids, such as succinic, malonic or maleic acids. Of the aromatic acids, those with only one benzene ring are preferred, particularly benzoic acid and its derivatives with methyl, hydroxyl, amine or carboxyl groups, such as p-aminobenzoic acid, salicylic acid or phthalic acid. In the process of the invention, these acids are reacted in the form of an anhydride thereof for reacting with the hydroxyl group of an esterified or free carboxyl-group ganglioside.

The invention also includes peracylated derivatives of gangliosides and their mixtures described above, with, however, free carboxyl functions. For these derivatives too, those acylated derivatives deriving from the acids described above are particularly important. Regarding also peracylated derivatives with free or esterified carboxylic functions, or in the form of amides, the ganglioside derivatives or groups A and B are particularly important, as are their mixtures, particularly those with acyl groups and those of the esters and amides previously mentioned. Therefore, one group of new ganglioside derivatives which is particularly preferred is that comprising ganglioside esters and amides and their peracylated derivatives in the hydroxyl groups as well as such peracylated derivatives with carboxyl functions of the said gangliosides in free form. In these derivatives the ester groups are derived from alcohols formed by the group consisting of aliphatic alcohols with a maximum of 6 saturated carbon atoms, unsubstituted or substituted by hydroxyl, alkoxyl groups with a maximum of 4 carbon atoms, aminic, alkylaminic or dialkylaminic groups with a maximum of 4 carbon atoms in the alkyl groups, carboxylic groups, carbalcoxylic groups with a maximum of 4 carbon atoms in the alkyl residue, and the corresponding alcohols with a double bond at the most, and araliphatic alcohols with only one benzene ring, unsubstituted or substituted by between 1 and 3 methyl groups, cycloaliphatic or aliphatic-cycloaliphatic alcohols with a cyclohexane ring, unsubstituted or substituted by between 1 and 3 methyl groups and a maximum of 4 carbon atoms in the aliphatic part, and tetrahydrofuranol and tetrahydropyranol.

The amide groups in the most preferred derivatives are derived from ammonia or alkylamines, dialkylamine or alkyleneamines, with a maximum of 6 carbon atoms in the alkyl groups and between 4 and 8 carbon atoms in the alkylene groups and in which the alkyl or alkylene groups may be interrupted in the carbon atom chain by heteroatoms chosen from the group formed by nitrogen, oxygen and sulphur, as the group may be iminic —NH in the case of the presence of a nitrogen atom substitued by an alkyl with a maximum of 4 carbon atoms and/or may be substituted by groups chosen from the group formed by aminic, alkylaminic or dialkylaminic groups with a maximum of 4 carbon atoms in the alkyl groups, or by hydroxyl or alkoxyl groups with a maximum of 4 carbon atoms in the alkyl groups, or by araliphatic amines with only one benzene ring which may be substituted by a maximum of 3 methyl groups and with a maximum of 4 carbon atoms in the aliphatic part.

The acyl groups esterifying the hydroxyls in these most preferred derivatives derive from aliphatic acids, saturated or unsaturated with a maximum of 6 carbon atoms, which may also be substituted by a function chosen from the groups comprising hydroxyl, aminic and carboxyl groups, and their salts. This group of most preferred derivatives, and especially that of the gangliosides of groups A and B mentioned above and also the derivatives of ganglioside mixture, of groups A and B for example (with the functional groups specified here) are of particular interest as ingredients for the pharmaceutical preparations according to the present invention. Of the specific new compounds of the present invention, particularly important for pharmaceutical preparations, the following derivatives are important:

the ethyl ester of ganglioside $G_{M1}$
the propyl ester of ganglioside $G_{M1}$
the isopropyl ester of ganglioside $G_{M1}$
the normal butyl ester of ganglioside $G_{M1}$
the isobutyl ester of ganglioside $G_{M1}$
the tertiary-butyl ester of ganglioside $G_{M1}$
the cyclohexyl ester of ganglioside $G_{M1}$
the esters corresponding to those listed here containing the ganglioside $G_{D1b}$ in place of ganglioside $G_{M1}$
the esters listed above containing the ganglioside $G_{D1a}$ in place of ganglioside $G_{M1}$
the esters listed here containing the ganglioside $G_{T1b}$ in place of ganglioside $G_{M1}$
the peracetylates of the esters named above
the perpropionilates of the esters named above
the per-n-butyrrilates of the esters named above
the permaleinylates of the esters named above
the permalonylates of the esters named above
the persuccinylates of the esters named above
the peracetylates of gangliosides $G_{M1}$, $G_{D1b}$, $G_{D1a}$, $G_{T1b}$
and the perpropionylates, the per-n-butyrrylates, the permalonylates, the persuccinylates and the permaleinylates of the same gangliosides
the amide of ganglioside $G_{m1}$
the amide of ganglioside $G_{D1a}$
the amide of ganglioside $G_{D1b}$
the amide of ganglioside $G_{T1b}$
the methylamide, the ethylamide, the propylamide of gangliosides $G_{M1}$, $G_{D1b}$, $G_{D1a}$, $G_{T1b}$ and also the amides of these gangliosides deriving from dimethylamine, diethylamine, pyrrolidine, piperidine, piperazine, morpholine, thiomorpholine, the peracetylates, the perpropionylates, the per-n-butyrrilates, the permalonylates, the permaleinylates and the persuccinylates of the amides mentioned just above, the methyl, ethyl, propyl, isopropyl, tertiary butyl, benzyl, allyl, ethoxycarbonylmethyl esters of the ganglioside mixtures containing $G_{M1}$, $G_{D1a}$, $G_{D1b}$, $G_{T1b}$, as principal gangliosides and especially the mixture obtained according to the illustrated example No. 2, unsubstituted amide, methylamide, ethylamide, benzylamide, isopropylamide, dimethylamide, diethylamide, dimethylaminopropylamide, dimethylaminoethylamide, ethanolamide of gangliosides containing $G_{M1}$, $G_{D1a}$, $G_{D1b}$, $G_{T1b}$, as principal gangliosides and especially the mixture obtained according to illustrated example No. 2, the peraceylated, per-n-butyrrylated, perpropionylated, permaleinylated, permalonylated, persuccinylated derivatives of a ganglioside mixture containing $G_{M1}$, $G_{D1a}$, $G_{D1b}$, $G_{T1b}$ as principal gangliosides and especially the mixture obtained according to illustrated Example No. 2.

From the new compounds according to the present invention with free carboxyl functions, such as peracylates of gangliosides, for instance those of groups A and B, metallic salts may be prepared, which also form part of the invention. Metallic salts may also be prepared from other derivatives of the invention which possess a free acid function, such as peracylated esters or amides with bibasic acids. Furthermore, salts obtained by acid addition of ganglioside derivatives, containing a free amine function also form part of the invention, such as esters with aminoalcohols. Of the metallic salts, particularly preferred are those which can be used in therapy, such as the salts of alkaline and alkaline earth metals, such as potassium, sodium, ammonium, calcium, magnesium, salts, or salts of earth metals such as aluminum, but also the salts with organic bases, such as primary, secondary or tertiary aliphatic, aromatic or heterocyclic amines, such as methylamine, ethylamine, propylamine, piperidine, morpholine, ephedrine, furfurylamine, choline, ethylendiamine, aminoethanol.

Of the acids able to give salts with ganglioside derivatives by acid addition according to the invention, particulary preferred are the hydracids, such as hydrochloric acid, bromhydric acid, the phosphoric acids, sulphuric acid, the lower aliphatic acids with a maximum of 7 carbon atoms, such as formic, acetic or propionic, succinic or maleic acid. Unusable therapeutic acids or bases, such as picric acid, can be used for the purification of the new ganglioside derivatives and form part of the invention. Due to the close connection between the new derivatives in free form and in the form of their salts, this description of the invention is to be considered as encompassing both forms, unless the contrary is expressly stated.

The new ganglioside esters and amides of this invention generally represent amorphous, colourless, or greyish powders which can be quite successfully dissolved in water and polar solvents, such as lower aliphatic alcohols, for instance, methyl, ethyl or propyl alcohol, or also in ketones, such as acetone or in amides, such as dimethylformamide or in sulphoxides, such as dimethylsulphoxide, or ethers, such as dioxane or tetrahydrofurane. Solubility in water is, however, considerably reduced in the derivatives acylated at the hydroxyl groups, while it is increased in the organic solvents mentioned above. For the manufacture of the pharmaceutical preparations in the form of solutions for parenteral use, the most suitable solvents will be chosen each time, according to the more or less hydrophil or lipophil character of the new derivatives.

METHODS OF PREPARATION

The present invention also includes preparation methods for the new ganglioside derivatives described above or for those already known. These methods are on the one hand the conventional, already known methods for the preparation of the new esters and amides of carboxylic acids and for the acylation of hydroxyl groups for the preparation of the new acyl derivatives, except for those methods which would have the effect of altering the ganglioside base, such as those making use of highly acidic agents or those which in any case are carried out in alkaline or acid hydrolyzing conditions, or also those methods which may cause undesired alkylation of the hydroxyl groups of the saccharide part. On the other hand the invention also includes a new preparation method for both new and known esters, starting with the internal esters of gangliosides as described hereafter.

As the invention includes the preparation of ganglioside derivatives with esterified carboxyl functional groups or in the form of amides and also the acylated derivatives in the hydroxyl groups of these derivatives, on the one hand it is possible in this way to modify the carboxyl functions both of free gangliosides, that is with free hydroxyl functions, and of gangliosides with already acylated hydroxyl functions. On the other hand, it is possible to acylate the hydroxyl functions in already esterified derivatives or in the amide derivatives. It is also possible, according to the invention, to acylate the hydroxyl functions alone, leaving the carboxyl functions free. Therefore, according to the present invention, a ganglioside or one of its peracylated derivatives is esterified in the carboxyl groups, or these are converted to amides, or the hydroxyl groups of these ganglioside derivatives or the gangliosides with free carboxyl functions are acylated. Should it be desired, salifiable compounds obtained are converted into their salts.

1. Esterification of carboxyl groups

Of the methods known for the preparation of carboxylic esters, mentionable are those used for the preparation of the already known methyl esters of gangliosides $G_{M1}$ and $G_{M3}$ described in the above mentioned article in Journal of Lipid Research, 21, 642–645 (1980). According to this article, it is possible to obtain the esters of the carboxyl groups of gangliosides by reacting the latter with an alcohol of which the ester is to be obtained in the presence of an ionic exchanger, for example, a resin such as Dowex 50. The yield is limited due to the simultaneous formation of internal esters and the longer reaction times (2–3 days).

The same method is used, for example, also in the above mentioned article in Methods of Enzymology, 50, 137–140 (1978) for the preparation of the methyl esters of $G_{M3}$ ganglioside. This kind of partial esterification can clearly also be obtained, albeit with an even lower yield, in the absence of resins. Apart from Dowex 50 resin, other acid ionic exchangers can also be used, having the function of converting gangliosides which, as already stated, are generally present and especially in extracts in the form of salts, particularly sodium salts, in free gangliosides. This operation of conversion of ganglioside salts into free gangliosides is suitable also for all the other conventional methods described herein, for functionally modifying the carboxylic function, such as those for the preparation of amides. However, the best method described in the above mentioned article consists of esterifying the carboxyl or carboxyls present in gangliosides by passing an alcoholic solution of the desired alcohol on a resin such as Dowex $-50W \times 8$ (100–200 mesh H form) and treating the eluate dissolved in the same alcohol with the corresponding diazomethane. In the specific case described, the esters of gangliosides $G_{M1}$ and $G_{M3}$ were prepared by treatment in this way with methanol and diazomethane, giving a very good yield.

Another good preparation method of esters of ganglioside carboxyls consists of treating a ganglioside metallic salt with an etherifying agent. Salts of alkaline or alkaline earth metals are used, or also any other metal salt. As an etherifying agent, those per se known in literature may be used, especially the esters of various inorganic acids, or organic sulphonic acids, such as the hydracids, in other words the hydrocarbon halogenides, such as methyl, ethyl iodide etc., or the neutral or acid sulphates of hydrocarbons, sulphites, carbonates, silicates, phosphites or hydrocarbon sulphonates, such as benzo or p-toluol-sulphonate of methyl or chlorosulphonate of methyl or ethyl. The reaction can be carried out in a suitable solvent, such as an alcohol, preferably the one corresponding to the alkyl group which is to be introduced into the carboxyl group, but nonpolar solvents may also be used, such as ketones, ethers, such as dioxane or dimethylsulphoxide.

A new method which is characteristic of the present invention for the preparation of ganglioside esters, and which may be used both for the preparation of the new gangliosides according to the invention, and also for the preparation of the already known esters, consists of treating an internal ganglioside ester with a mixture of the desired alcohol with one of its corresponding alcoholates. The reaction can be carried out at a temperature corresponding to the boiling point of the alcohol. Lower temperatures may also be used but in this case the reaction times are longer. It is also possible, relinquishing however the very good yield and short reaction times, to treat the internal ester with just the relevant alcohol, preferably at a temperature corresponding to boiling point of the same. The internal esters are described for example in the above mentioned Belgian Pat. No. 894024 and U.S. Pat. No. 4,476,119.

As alcoholates it is preferable to use alkaline metal alcoholates, especially sodium alcoholate.

2. Preparation of amides

The new ganglioside amides according to the present invention can be prepared by per se known methods, especially by the following methods.

(a) reaction of the internal esters of gangliosides with ammonia or with amines.

(b) reaction of the carboxyl esters of gangliosides with ammonia or with amines.

(c) reaction of the ganglioside acids with the carboxyl groups activated with ammonia or amines.

Reaction (a), which has been described in the case of the preparation of the amide of ganglioside $G_{M3}$ (see above) can be effected by direct treatment, with or without solvent, of the internal ganglioside ester with ammonia or with the amine whose amide is to be prepared. The reaction can be effected at quite low temperatures, such as from $-5°$ to $+10°$ C., but room temperature or higher is preferable, for instance between 30° and 120° C. As solvents, ketones, aromatic hydrocarbons, dimethylformamide, dimethylsulphoxide, dioxane, or tetrahydrofurane can be used.

Reaction (b) is effected preferably in the conditions described for (a). Apart from the esters described for the present invention, other esters may also be used, such as esters with phenols.

For activation of the carboxyl group in the reaction according to (c), methods per se known in peptide chemistry are used, avoiding those involving conditions which are too acid or basic which would cause disruption of the ganglioside molecule. If the starting gangliosides are in the form of sodium salts for example, it is advisable to first treat the salt with an ion exchanging resin of the Dowex type, or another acid ion exchanger. For example, it is possible to use the method of condensation in the presence of carbodiimides such as dicyclohexylcarbodiimide, benzylisopropylcarbodiimide or benzylethylcarbodiimide, in the presence of 1-hydroxybenzotriazol or condensation in the presence of N,N'-carbonyldiimidazol.

3. Acylation of the hydroxyl groups

Acylation of the hydroxyl groups of the saccharide, sialic part and of the ceramide also occurs in a way which is per se already known, for example by acylation with a halogenide or an anhydride of the acid being used for acylation, preferably in the presence of a tertiary base, such as pyridine or collidine. The reaction may take place at a low temperature, such as room temperature, leaving the acid derivative, such as anhydride, to react for quite a long time, 12 to 24 hours for example, or at a slightly higher temperature such as 50°-100° C., for a few hours.

The invention also includes modifications in the preparation procedures of the new derivatives, in which a procedure is interrupted at any given point or in which preparation is begun with an intermediate compound and the remaining stages are carried out, or in which the starting products are formed in situ.

EXAMPLE 1

Methyl ester of the ganglioside $G_{M1}$ 5 g of the internal ester of the ganglioside $G_{M1}$ (3.27 mM) are dissolved in 200 ml of an anhydrous mixture of methylene chloride and methanol 4:1. 176 mg (3.27 mM) of sodium methylate dissolved in 50 ml of anhydrous methanol are added and the mixture is refluxed for 2 hours. At the end of the reaction the mixture is neutralized with Dowex AG 50×8 anhydrous resin (H+form), the resin is separated by filtration and washed with methanol and the solution is evaporated by drying. The residue is gathered in 50 ml of methylene chloride/methanol 1:1 and the reaction product is precipitated by pouring it into 250 ml of acetone. The raw product (4.9 g) is purified by preparative high pressure chromatography with 60H Merck silica gel, using as solvent a mixture of chloroform/methanol/isopropanol/ammonium carbonate at 2% 1140:820:180:140. The pure fractions are gathered, evaporated by drying, redissolved in 15 ml of chloroform/methanol 1:1 and the product is precipitated with 75 ml of acetone. This product represents the methyl ester of the ganglioside $G_{M1}$. Yield 4.2 g.

IR spectroscopy carried out on KBr pellets shows the typical bond of the ester at 1750 cm$^{-1}$. Chromatography on silica gel plates with chloroform/methanol/CaCl$_2$ at 0.3% 55:45:10 and determined with Ehrlich reagent (Rf 0.72) showed the product to be a unitary compound and free from the internal ester used as starting product (Rf 0.75) and from the ganglioside $G_{M1}$ (Rf 0.65). By treatment with an 0.1N solution of Na$_2$CO$_3$ at 60° for an hour, the ester bond is split, giving the primary product, $G_{M1}$.

EXAMPLE 2

Preparation of a ganglioside mixture (GA mixture) by extraction from bovine brain tissue and of the corresponding mixture of internal esters (to be used in the various subsequent Examples)

Bovine brain cortex, removed from the animal, is homogenized in phosphate buffer at pH 6.8; 6 volumes of tetrahydrofuran are added and the resulting mixture is centrifuged. The supernatant is re-extracted twice with tetrahydrofuran. After contrifugation the non-polar materials are removed by separation with ethyl ether and the aqueous-tetrahydrofuranic layer is introduced on an ionic exchange column balanced with 50% ethanol. Barium hydroxide and four volumes of ice cold ethanol are added to the effluent from the column.

After 18 hours in cold conditions, the precipitate is gathered and then slightly acidified with hydrochloric acid after solution in water. The solution thus obtained is dialyzed and freeze-dried. The yield at this point is of about 0.6 mg of raw ganglioside mixture per gram of nervous tissue used. The freeze-dried powder is dispersed in 20 volumes of chloroform-methanol 2:1, the solution obtained is filtered until it is perfectly clear, and then separated by adding 0.2 volumes of a solution of potassium chloride in water at 0.88%.

The upper layer is separated, dialyzed and freeze-dried. The final yield is of about 0.3 mg of purified mixture of ganglioside salts per gram of brain tissue.

5 grams of a mixture obtained according to the method described above are dissolved in 50 ml of DMSO. 4 grams of styrene-type, anhydrous resin (sulphonic acid) (50–100 mesh, H+ form) are added to the mixture and the resulting system is agitated for 30 minutes at room temperature. This treatment with an ionic exchange resin transforms all salified carboxyl groups. Complete transformation is confirmed by a suitable method of physical analysis, such as atomic absorption. The resin is then filtered under suction and the solution is treated with 1.5 g of dicyclohexylcarbodiimide and left to rest for an hour. The precipitated dicyclohexylurea is removed by filtration and the resulting solution is treated with 100 ml of O causing precipitation of the internal ganglioside esters produced.

The yield is of 4.6 g of mixture of internal esters (about 90–95% of the theoretical value). The presence of internal ester derivatives is confirmed by infrared spectroscopy and by then layer chromatography. IR Spectroscopy on KBr pellet: the esterifying lactonic bond produces a band at 1750 cm$^{-1}$. Thin layer chromatography: on silica gel plate, developing solvent: CHCl$_3$/MeOH/CaCl$_2$ 0.3% (55:45:10, v/v/v), the Rf of the internal ester mixture is between 0.7 and 0.85. The Rf of the final products is greater than the Rf of the mixture of starting substance; consequently chromatography shows the absence of starting material. By treatment with a solution of 0.1N of Na$_2$CO$_3$ at 60° for an hour the ester bonds are split and it is possible to obtain the primary mixture of the starting gangliosides.

The ganglioside mixture obtained can be fractioned in various portions substantially representing pure gangliosides (in the sense used in the general description), using silicic acid columns and eluting with a mixture of methanol-chloroform. In this way an average composition is obtained of about 40% of the ganglioside $D_{D1a}$, 21% of the ganglioside $G_{M1}$, 19% of the ganglioside $G_{T1b}$ and 16% of the ganglioside $G_{D1b}$.

EXAMPLE 3

Mixture of methyl esters of a ganglioside mixture 5 g of a mixture of internal esters of a mixture of gangliosides (obtained by extraction from bovine brain tissue as described in Example 2) are dissolved in 200 ml of an anhydrous mixture of methylene chloride and methanol 4:1. 318 mg (5.86 mM) of sodium methylate dissolved in 50 ml of anhydrous methanol are added and the mixture is refluxed for 2 hours. The raw product of the reaction is then isolated as described in Example 1 (4.9 g). The raw product is then purified by chromatography on Sephadex-DEAE acetate form A-25, using as solvent a mixture of chloroform/methanol/water 30:60:8. The mixed neutral fractions are evaporated, dialyzed in water, evaporated again by drying, the residues are dissolved in 15 ml of chloroform/methanol 1:1 and the product is precipitated with 75 ml of acetone. Yield: 4.3 g. IR spectroscopy, carried out on KBr pellets, showed the typical bond of the ester at 1750 cm$^{-1}$. Chromatography carried out as described in Example 1 showed the product which represents the mixture of methyl esters of the gangliosides, to have an Rf of 0.72-0.85 (Rf of the ganglioside mixture, 0.2-0.70).

Complete transesterification may be confirmed by determining the molecular proportion between the alkoxy and sialic groups which are obtained by quantitative "head space" gas-chromatography of the methyl alcohol released after treatment with 0.1N solution of $Na_2CO_3$ at 60° for one hour, causing the splitting of all the ester bonds, and with Svennerholm's method for determination of N-acetylneuraminic acid.

EXAMPLE 4

Ethyl ester of the ganglioside $G_{M1}$

The ethyl ester of $GM_1$ is prepared and isolated in the same manner as for the methyl ester in Example 1, using however ethyl alcohol and sodium ethylate in the place of methyl alcohol and sodium methylate, and using the same molar quantities of internal ester and ethylate as in Example 1. Washing of the Dowex resin is effected with ethyl alcohol and the residue obtained by evaporation of the filtered substance is dissolved in 50 ml of methylene/chloride ethanol 1:1. The yield in raw product is 4.9 g. Purification is also carried out as in Example 1. Yield of the ethyl ester of purified $G_{M1}$ ganglioside: 4.3 g. Chromatographic analysis of the product carried out in the same way as in Example 1 shows the presence of a unitary compound with an Rf of 0.80, and the absence of $G_{M1}$ ganglioside and its internal ester (Rf 0.65 and 0.75, respectively). Hydrolysis with $NaCO_3$ as described in Example 1 produces the ganglioside $G_{M1}$. IR spectroscopic examination on KBr pellets shows the typical band of the ester at 1750 cm$^{-1}$.

EXAMPLE 5

Mixture of ethyl esters of a mixture of gangliosides

The mixture of ethyl esters is prepared and isolated in the same way as for the mixture of methyl esters of Example 3, using however ethyl alcohol and sodium ethylate instead of methyl alcohol and sodium methylate, and using 5 g of internal ester mixture and 318 mg (5.86 mM) of sodium ethylate.

Washing of the Dowex resin is carried out with ethyl alcohol and the residue obtained by evaporation of the filtered substance is dissolved in 50 ml of chloroform/ethanol 1:1. The yield in raw product is 4.9 g. Purification is also carrier out as in Example 3. The yield in purified ethyl ester mixture: 4.5 g. IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.50-0.75 (ganglioside mixture 0.20-0.60).

Complete transesterification is demonstrated in the same way as described in Example 3.

EXAMPLE 6

Isopropyl ester of the ganglioside $G_{M1}$

This derivative is prepared and isolated in the same way as for the methyl ester in Example 1, using however isopropyl alcohol and sodium isopropylate instead of methyl alcohol and sodium methylate, and using the same molar quantities of internal ester and isopropylate as in Example 1. Washing of the Dowex resin is effected with isopropyl alcohol and the residue obtained by evaporation of the filtered substance is dissolved in 50 ml of methylene chloride/isopropanol 1:1. The yield in raw product is 4.9 g. Purification is also carried out as in Example 1. Yield in isopropyl ester of purified $G_{M1}$ ganglioside: 4.2 g.

Chromatographic analysis of the product, carried out in the same way as in Example 1, shows the presence of a unitary compound with an Rf of 0.85 and the absence of $G_{M1}$ ganglioside or its internal ester. Hydrolysis with $NA_2CO_3$ as described in Example 1 produces the ganglioside $G_{M1}$. IR spectroscopy on KBr pellets shows the typical ester band at 1750 cm$^{-1}$.

EXAMPLE 7

Mixture of isopropyl esters of a ganglioside mixture

This derivative mixture is prepared and isolated in the same way as for the mixture of methyl esters in Example 3, using however isopropyl alcohol and sodium isopropylate instead of methyl alcohol and sodium methylate, and using 5 g of internal ester mixture and 537 mg (6.52 mM) of sodium isopropylate. Washing of the Dowex resin is effected with isopropyl alcohol and the residue obtained by evaporation of the filtered substance is dissolved in 50 ml of chloroform/isopropanol 1:L. The yield in raw product is 4.9 g. Purification is also carried out as in Example 3, using however as chromatographic eluent a mixture of chloroform/isopropyl alcohol/water 20:60:8. Yield in mixture of purified isopropyl esters: 4.3 g.

Chromatographed by the method described in Example 5, the product shows an Rf of 0.40-0.78 (ganglioside mixture 0.20-0.60). IR spectroscopy carried out on KBr pellets, shows the typical ester band at 1750 cm$^{-1}$. Complete transesterification is demonstrated as described in Example 3.

EXAMPLE 8

Tertiary butyl ester of the ganglioside $GM_1$

This derivative is prepared and isolated in the same way as for the methyl ester in Example 1, using however tertiarybutyl alcohol and sodium tertiarybutylate instead of methyl alcohol and sodium methylate, and using the same molar quantities of internal esters and tertiarybutylate as in Example 1. Washing of the Dowex resin is effected with tertiarybutyl alcohol and the residue obtained by evaporation of the filtered substance is dissolved in 50 ml of methylene chloride/tertiarybutanol 1:1. The yield in raw product is 4.9 g. Yield in tertiarybutyl ester of purified $G_{M1}$ ganglioside: 4.1 g.

Chromatographic analysis of the product, carried out in the same way as in Example 1, shows the presence of a unitary compound with an Rf or 0.71 and the absence of $G_{M1}$ ganglioside and of its internal ester. Hydrolysis with $Na_2CO_3$ as described in Example 1 produces the ganglioside $G_{M1}$. IR spectroscopy on KBr pellets shows the typical ester band at 1750 cm$^{-1}$.

EXAMPLE 9

Mixture of tertiarybutyl esters of a mixture of gangliosides

This mixture is prepared and isolated in the same way as for the mixture of methyl esters in Example 3, using however tertiarybutyl alcohol and sodium tertiarybutylate instead of methyl alcohol and sodium methylate, and using 5 g of internal ester mixture and 628.6 mg (6.52 mM) of sodium tertiarybutylate. Washing of the Dowex resin is effected with tertiarybutyl alcohol and the residue obtained by evaporation of the filtered substance is dissolved in 50 ml of chloroform/tertiarybutanol 1:1. The yield in raw product is 4.9 g. Purification is also carried out as in Example 3, using however as chromatographic eluent a mixture of chloroform/tertiarybutyl alcohol 1:1. Yield in purified tertiarybutyl esters: 4.1 g. IR spectroscopy carried out on KBr pellets shows the typical ester bond at 1750 cm$^{-1}$. Chromatographed by the method described in Example 5, the product shows an Rf of 0.25–0.70. Complete reaction is demonstrated as described in Example 3.

EXAMPLE 10

Benzyl ester of the ganglioside $G_{M1}$ 5 g of potassium salt of the ganglioside $G_{M1}$ (3.14 mM) are dissolved in 50 ml of DMSO and 1.58 g (12.5 mM) of benzyl chloride and 2.08 g (12.5 mM) of KI are added to the solution. It is left to react in nitrogen for 24 hours at 25° C. At the end of the reaction the solution is partitioned with n-butanol/water 2:1 to eliminate the DMSO and the salts. The butanol solution is evaporated by drying and the residue is gathered in 50 ml of chloroform/benzyl alcohol 1:1 and the reaction product is precipitated with 250 ml of acetone.

The raw product thus obtained (5.3 g) is then purified by preparative chromatography on silica gel plates using as solvent a mixture of chloroform/methanol/water 65:32:7.

The pure fractions are mixed, evaporated, redissolved in 15 ml of chloroform/isopropanol 1:1 and the product is precipitated with 75 ml of acetone. Pure benzyl ester yield: 4.8 g.

IR spectroscopy, carried out on KBr pellets, shows the typical ester band at 1750 cm$^{-1}$ and UV spectroscopy examination, carried out in absolute ethyl alcohol shows three maximums at 250, 255 e 261 nM.

Chromatographed on silica gel plates with chloroform/methanol/CaCl$_2$ at 0.3% 60:35:8 and with chloroform/methanol/ammonia 2.5N 55:45:12 and determined with Ehrlich reagent, the product proves to be unitary with an Rf of 0.65 and 0.53 respectively and to be free from $G_{M1}$ starting product (Rf respectively and to be free from $G_{M1}$ starting product (Rf 0.40 and 0.45 respectively).

Treatment with 0.1N solution of Na$_2$CO$_3$ at 60° for an hour, causes the splitting of the ester bond giving the starting products ($G_{M1}$ and benzyl alcohol).

EXAMPLE 11

Mixture of benzyl esters of a mixture of gangliosides 5 g of a mixture of salified gangliosides (potassium salts) obtained by extraction from bovine brain tissue as described in Example 2 and by subsequent substitution of sodium with potassium (ionic exchange) are dissolved in 100 ml of DMSO and 3.3 (26.0 mM) of benzyl chloride and 216 g (13.0 mM) of KI are added to the solution. The mixture is left to react in nitrogen for 48 hours at 25° C. At the end of the reaction the solution is partitioned with n-butanol/H$_2$O 2:1 to eliminate the DMSO and the salts. The butanol solution is evaporated by drying and the residue is gathered in 50 ml of chloroform/benzyl alcohol 1:1 and the product is precipitated with 250 ml of acetone. The raw product thus obtained (5.6 g) is then purified by chromatography with Sephadex—DEAE, acetate form, using as solvent a mixture of chloroform/methanol/water 30:60:8.

The eluted neutral fractions are mixed, freed of solvent by evaporation and the residue is gathered with 15 ml of chloroform/isopropanol 1:1 and the mixture of purified benzyl esters is precipitated with 75 ml of acetone. Yield 4.9 g.

IR spectroscopy, carried out on KBr pellets, shows the typical ester bond at 1750 cm$^{-1}$ and UV spectroscopy examination carried out in absolute ethyl alcohol, shows three maximums at 250, 255 and 261 nM.

Chromatographed on silica gel plates with chloroform/methanol/CaCl$_2$ at 0.3% 60:25:8 and with chloroform/methanol/ammonia 2.5N 55:45:10 and determined with Ehrlich reagent, the product proves to possess an Rf varying between 0.40 and 0.70 and between 0.29 and 0.53 respectively (for the original ganglioside mixture 0.05–0.40 and 0.12–0.46 respectively).

Complete reaction is demonstrated as described in Example 3.

EXAMPLE 12

Allyl ester of the ganglioside $G_{M1}$ 5 g of potassium salt (3.14 mM) of the ganglioside $G_{M1}$ are dissolved in 50 ml of DMSO and 453.7 mg (3.75 mM) of allyl bromide and 625 mg (3.75 mM) of KI are added to the solution. It is left to react for 48 hours at 25° C.

At the end of the reaction the solution is partitioned with n-butanol/H$_2$O 2:1 to eliminate the DMSO and the salts. The butanol solution is evaporated by drying and the residue is gathered in 50 ml of chloroform/methanol 1:1 and the product is precipitated with 250 ml of acetone.

The raw product thus obtained (5.1 g) is then purified by preparative column chromatography on silica gel using as solvent a mixture of chloroform/methanol/water 60:35:8.

The pure fractions are mixed, evaporated, redissolved in 15 ml of chloroform/isopropanol 1:1 and the product is precipitated with 75 ml of acetone. Pure allyl ester yield: 4.5 g.

IR spectroscopy, carried out on KBr pellets, shows the typical ester band at 1750 cm$^{-1}$.

Chromatographed on silica gel plates with chloroform/methanol/CaCl$_2$ at 0.3% 60:40:9 and with chloroform/methanol/ammonia 2.5N 55:45:10 and determined with Ehrlich reagent, the product proves to be a unitary compound with Rf of 0.56 and 0.39 respectively and to be free from starting ganglioside $G_{M1}$ (Rf 0.40 and 0.42 respectively).

Treatment with a solution of Na$_2$CO$_3$ 0.1N at 60° for an hour causes the splitting of the ester bond, giving starting ganglioside GM$_1$ and allyl alcohol.

EXAMPLE 13

Ethoxycarbonylmethyl ester of the ganglioside GM$_1$ 5 g of potassium salt (3.14 mM) of the ganglioside $G_{M1}$ are dissolved in 50 ml of DMSO and 2.12 g (12.5 mM) of ethylmonobromoacetate and 2.08 g (12.5 mM) of KI are added to the solution. It is left to react in nitrogen for 24 hours at 25° C. The solution is then partitioned with n-butanol/water 2:1 to eliminate the DMSO and the salts. The butanol solution is evaporated by drying and the residue is gathered with 50 ml of chloroform/methanol 1:1 and the product is precipitated with 250 ml of acetone. Yield 4.8 g.

The raw product is purified by preparative column chromatography on silica gel, using as solvent a mixture of chloroform/methanol/water 60:32:7. The pure fractions are mixed, evaporated by drying, and the residue dissolved in 15 ml of chloroform/methanol 1:1 and the ethoxycarbonylmethyl ester is precipitated with 75 ml of acetone. Yield: 2.4 g.

IR spectroscopy, carried out on KBr pellets, shows the typical ester band at 1750 cm$^{-1}$.

Chromatographed on silica gel plates with chloroform/methanol/CaCl$_2$ at 0.3% 60:35:8 and determined with Ehrlich reagent, the product proves to be a unitary compound with Rf of 0.64 and to be free from starting compound G$_{M1}$ (Rf 0.40).

Treatment with 0.1N solution of Na$_2$CO$_3$ at 60° C. for an hour causes splitting of the ester bond, giving the original ganglioside G$_{M1}$.

EXAMPLE 14

Amide of the ganglioside G$_{M1}$ 5 g of the internal ester of the ganglioside G$_{M1}$ (3.27 mM) are suspended in 100 ml of anhydrous isopropyl alcohol. The suspension is maintained in agitation at a low temperature (−5°) and dry ammonia is then bubbled through it in anhydrous conditions for 3 hours.

At the end of the reaction, the solvent is eliminated by evaporation and the residue is gathered in 50 ml of chloroform/methanol 1:1 and the product is precipitated with 250 ml of acetone.

The raw product (4.9 g) is treated with 100 ml of Na$_2$CO$_3$ 1% for 30 minutes at 25° C. to hydrolyze residue ester groups, dialyzed in water, evaporated by drying in vacuum and then purified by a preparative column chromatography on silica gel, using as first solvent a mixture of chloroform/methanol/H$_2$O 60:40:9 and as second solvent a mixture of chloroform/methanol/H$_2$O 55:45:10. The pure, eluted mixed fractions are evaporated by drying, the residue is dissolved in 15 ml of chloroform/methanol 1:1 and the amide is precipitated with 75 ml of acetone. Yield: 4.8 g.

Chromatographed on silica gel plates with chloroform/methanol/ammonia 4N 55:45:10 and chloroform/methanol/CaCl$_2$ at 0.3% 55:45:10 and determined with resorcinol reagent, the product proves to be a unitary compound (Rf 0.10 and 0.32 respectively) and to be free from G$_{M1}$ (Rf 0.35 and 0.65 respectively).

EXAMPLE 15

Mixture of the amides of a ganglioside mixture 5 g of the mixture of internal esters of gangliosides described in Example 2 are reacted with ammonia as in Example 14 and precipitated with acetone also as described in Example 14. After a hydrolytic treatment with NaCO$_3$ as described in the previous Example, the raw product is purified as follows:

The product obtained by hydrolysis is dialyzed against water, the solution is vacuum evaporated, the residue is gathered with 50 ml of chloroform/methanol/H$_2$O 30:60:8 and then purified by preparative chromatography with Sephadex DEAE A-25, acetate form using as solvent a mixture of chloroform/methanol/water 30:60:8.

The eluted neutral fractions are evaporated until dry, dialyzed, evaporated until dry once more, dissolved in 15 ml of chloroform/methanol 1:1 and the mixture of amides is precipitated with 75 ml of acetone. Yield: 4.8 g.

IR spectroscopy no longer shows the typical ester band at 1750 cm$^{-1}$.

Chromatographed on silica gel plates with chloroform/methanol/ammonia 4N 55:45:10 and chloroform/methanol/CaCl$_2$ at 0.3% 55:45:10 and determined with resorcinol reagent, the product has an Rf varying between 0.01 and 0.10 and between 0.55 and 0.45 respectively (mixture of original ganglioside, Rf 0.15–0.70 and 0.20–0.70 respectively).

EXAMPLE 16

Methylamide of the ganglioside G$_{M1}$ 5 g of internal ester of the ganglioside G$_{M1}$ (3.27 mM) are suspended in 25 ml of anhydrous methylamine in a recipient complete with reflux refrigerator at −25° C. in anhydrous conditions. The suspension is maintained in agitation at room temperature for 3 hours. At the end of the reaction the solvent is eliminated by evaporation and the residue is gathered with 50 ml of chloroform/methanol 1:1 and precipitated with 250 ml of acetone.

The raw product thus obtained (4.9 g) is treated with 100 ml of Na$_2$CO$_3$ 1% for 30 minutes at 25° C. to hydrolyze residue ester groups, and then dialyzed in water. The solution is evaporated until dry in vacuum and the residue is purified by preparative chromatography with Sephadex DEAE A-25, acetate form, using as solvent a mixture of chloroform/methanol/water 30:60:8.

The mixed neutral fractions are evaporated until dry, dialyzed, evaporated again, dissolved in 15 ml chloroform/methanol 1:1 and the methylamide is precipitated with 75 ml of acetone. Yield: 4.8 g.

IR spectroscopy did not show the typical ester band at 1750 cm$^{-1}$.

Chromatographed on silica gel plates with chloroform/methanol/ammonia 4N 55:45:10 and with chloroform/methanol/CaCl$_2$ at 0.3% 55:45:10 and determined with resorcinol reagent, the product proved to be a unitary compound with Rf of 0.13 and 0.72 respectively and to be free from G$_{M1}$ (Rf 0.35 and 0.65 respectively).

EXAMPLE 17

Mixture of methylamides of a ganglioside mixture 5 g of the internal ester mixture used in Example 15 is treated with methylamine as in the previous Example and the reaction product is treated and isolated in the same way as in that Example. The yield of pure product (mixture of methylamides of the ganglioside mixture used) is 4.8 g.

The Rf values determined as in the previous Example are 0.01–0.10 and 0.20–0.45 respectively (mixture of original gangliosides: Rf 0.15–0.70 and 0.20–0.70 respectively). The IR spectroscopic data are the same as those in the previous Example.

EXAMPLE 18

Ethylamide of the ganglioside G$_{M1}$

This derivative is prepared from 5 g of internal ester of the ganglioside G$_{M1}$ (3.27 mM) and from 25 ml of ethylamine in the same way as in Example 16 and the same purification method is also followed. A yield of 4.8 g of pure ethylamide of the ganglioside G$_{M1}$ is obtained.

The IR spectroscopic data are the same as for the methylamide in Example 16 and chromatographic examination in the same conditions as in that Example proved the product to be unitary and free from G$_{M1}$

EXAMPLE 19

Mixture of ethylamides of a ganglioside mixture

This derivative mixture is prepared with 5 g of the mixture of internal esters of gangliosides used in Example 17 and 25 ml of ethylamine in the same way as in Example 17, the same purification method is also used. A yield of 4.8 g of the mixture of ethylamides of the ganglioside mixture is obtained.

The Rf values determined by chromatography on silica gel plates with chloroform/methanol/ammonia 4N 55:45:10 and chloroform/methanol/CaCl$_2$ at 0.3% 60:35:8 and determined with resorcinol reagent proved to be 0.11–0.24 and 0.35–0.55 respectively (Rf of the original mixture of gangliosides 0.15–0.70 and 0.05–0.40 respectively).

EXAMPLE 20

Butyl-2-amide of the ganglioside $G_{M1}$ 5 g of the internal ester of the ganglioside $G_{M1}$ (3.27 mM) are dissolved in 25 ml of anhydrous pyridine. 12.5 ml of 2-butylamine are added to the solution and the mixture is kept in agitation in anhydrous conditions for 24 hours at 25° C.

At the end of the reaction the solvent is evaporated and the residue gathered with 50 ml of chloroform/methanol 1:1 and the reaction product is precipitated with 250 ml of acetone.

The raw product thus obtained (5.2 g) is then treated with 100 ml of Na$_2$CO$_3$ at 1% for 30 minutes at 25° C. in order to hydrolyze residue ester groups, dialyzed against water, the dialyzed solution is evaporated in vacuum until dry and the residue is purified by preparative chromatography on silica gel, using as solvent chloroform/methanol/water 110:40:6. The pure eluted fractions are mixed, the solution evaporated until dry, the residue dissolved in 15 ml of chloroform/isopropanol 1:1 and the butylamide precipitated with 75 ml of acetone. The yield is 4.7 g.

IR spectroscopy no longer shows the typical ester band at 1750 cm$^{-1}$.

Chromatography on silica gel plates with chloroform/methanol/ammonia 4N 60:40:9 and chloroform/methanol/CaCl$_2$ at 0.3% 60:35:8 and determined with resorcinol reagent, showed the product to be unitary and free from the ganglioside $G_{M1}$ with an Rf of 0.30 and 0.50 respectively (Rf of $G_{M1}$, 0.42 and 0.40 respectively).

EXAMPLE 21

Benzylamide of the ganglioside $G_{M1}$ 5 g of the internal ester (3.27 mM) of the ganglioside $G_{M1}$ are dissolved in 20 ml of anhydrous pyridine and 396 mg (3.27 mM) of benzylamine are added to the solution which is then kept in agitation in anhydrous conditions for 24 hours at room temperature.

At the end of the reaction the solvent is eliminated by evaporation and the residue is gathered with 50 ml of chloroform/methanol 1:1 and the product is precipitated with 250 ml of acetone.

The raw product thus obtained (5.1 g) is purified according to the procedure described in Example 16, giving a yield of 4.6 g of the pure benzylamide ganglioside.

IR spectroscopy no longer shows the typical ester band at 1750 cm$^{-1}$.

Chromatography on silica gel plates with chloroform/methanol/ammonia 4N 55:45:10 and chloroform/methanol/CaCl$_2$ at 0.3% 60:35:8 shows that the product is unitary and free from $G_{M1}$ and presents Rf of 0.32 and 0.69 (Rf of $G_{M1}$=0.35 and 0.40).

EXAMPLE 22

Mixture of benzylamides of a ganglioside mixture

This mixture is prepared starting with 5 g of the ganglioside mixture used in Example 2 and with 792 mg (7.4 mM) of benzylamine according to the procedure used in the previous Example for the preparation of the benzylamide of the ganglioside $G_{M1}$. Purification of the raw product obtained is also effected as in the previous Example. The yield is 4.8 g.

IR spectroscopy and chromatography on silica gel plates are carried out as in the previous Example. The Rf values are 0.10–0.42 and 0.55–0.71 respectively (primary ganglioside mixture, 0.01–0.15 and 0.05–0.40 respectively).

IR spectroscopy no longer shows the typical ester band at 1750 cm$^{-1}$.

EXAMPLE 23

Isopropylamide of the ganglioside $G_{M1}$ 5 g of the internal ester of the ganglioside $G_{M1}$ (3.27 mM) are dissolved in 25 ml of anhydrous isopropylamine and the mixture is kept in agitation in anhydrous conditions for 24 hours.

At the end of the reaction the solvent is evaporated and the residue is gathered in 50 ml of chloroform/methanol 1:1 and the product is precipitated with 250 ml of acetone.

The raw product (4.8 g) is treated with 100 ml of a solution of Na$_2$CO$_3$ at 1% for 30 minutes at 25° C. to hydrolyze residue ester bonds, and then dialyzed in water. The dialyzed solution is evaporated until dry and purified by preparative chromatography on silica gel using as solvent a mixture of chloroform/methanol/ammonia 2.5N 60:40:9. The pure eluted fractions are mixed, dissolved in 15 ml of chloroform/methanol 1:1 and the product precipitated in 75 ml of acetone. Chromatography on silica gel plates using as solvent chloroform/methanol/ammonia 2.5N 60:40:9 and chloroform/methanol/CaCl$_2$ at 0.3% 60:35:8 and determined with resorcinol reagent, shows the isopropylamide (4.2 g) to be unitary and free from $G_{M1}$ and to have Rf of 0.25 and 0.66 respectively (Rf of $G_{M1}$, 0.42 and 0.40 respectively).

IR spectroscopy no longer shows the typical ester band at 1750 cm$^{-1}$.

EXAMPLE 24

Dimethylamide of the ganglioside $G_{M1}$ 5 g of the internal ester of the ganglioside $G_{M1}$ (3.27 mM) are dissolved in 25 ml dimethylamine. The mixture is kept in agitation in anhydrous conditions at a low temperature (−5°) for 24 hours. At the end of the reaction the mixture is treated with Na$_2$CO$_3$ and purified as described in the previous Example, using however as first solvent for the chromatography chloroform/methanol/ammonia 2.5N 60:40:9 and as second solvent chloroform/methanol/water 60:40:9. The dimethylamide weighs 4.6 g.

Spectroscopic and chromatographic examinations are carried out as described in the previous Example. The product proves to be unitary with Rf of 0.20 and 0.46, respectively, and free from $G_{M1}$ (Rf 0.42 and 0.40 respectively). IR spectroscopy shows no ester band at 1750 cm$^{-1}$.

EXAMPLE 25

Mixture of dimethylamides of a ganglioside mixture

This mixture is prepared by starting with 5 g of the mixture of internal esters of the gangliosides described in Example 2 and with 20 ml of anhydrous dimethylamine according to the method in the previous Example. The subsequent treatment is also carried out as in the previous Example, except for the preparative chromatography, which is carried out on Sephadex A-25, acetate form, using as solvent a mixture of chloroform/methanol/water 30:60:8. The pure product weights 4.9 g.

IR spectroscopy and chromatography are effected as in the previous Example.

Rf values are 0.15–0.50 and 0.40–0.56 respectively (original ganglioside mixture, 0.15–0.60 and 0.05–0.40 respectively).

EXAMPLE 26

Diethylamide of the ganglioside $G_{M1}$

This compound is prepared in the same manner as the dimethylamide in Example 24, starting with 5 g of internal ester of the ganglioside $GM_1$ and with 25 ml of anhydrous diethylamine. Purification is carried out in the same manner as in Example 23. Yield: 4.7 g. Chromatographic examination carried out as in Example 23 shows the product to be unitary with Rf of 0.29 and 0.50 respectively and to be free from $G_{M1}$. IR spectroscopy shows no ester band at 1750 cm$^{-1}$.

EXAMPLE 27

Mixture of diethylamides of a ganglioside mixture

This mixture is prepared by starting with 5 g of a mixture of gangliosides of the internal esters used in Example 2 and 20 ml of anhydrous diethylamine according to the method in the previous Example. Purification is effected as for the dimethylamide of the mixture in Example 25. Yield: 5.0 g.

Rf values (determined as in the previous Example) are 0.18–0.55 and 0.43–0.60 respectively). IR spectroscopy shows no ester band at 1750 cm$^{-1}$.

EXAMPLE 28

Ethylmethylamide of the ganglioside $G_{M1}$

This compound is prepared in the same manner as in Example 24, starting with 5 g of $G_{M1}$ ganglioside and 25 ml of ethylmethylamine. Purification is also carried out as in the aforesaid Example. Yield: 4.7 g.

Chromatography on silica gel plates is effected as in Example 24 and the product proves to be unitary and free from $G_{M1}$. Rf=0.25 and 0.48 respectively. IR spectroscopy shows no typical ester band at 1750 cm$^{-1}$.

EXAMPLE 29

3-dimethylaminopropyl-1-amide of the ganglioside $G_{M1}$ 5 g of the internal ester of ganglioside $G_{M1}$ (3.27 mM) are dissolved in 20 ml of anhydrous pyridine and 675 mg (6.6 mM) of 3-dimethylaminopropyl-1-amine are added to the solution. The mixture is agitated at room temperature for 24 hours. The product is isolated as in the previous Example and purified as in Example 28. Yield of 3-diamethylaminopropyl-1-amide: 4.9 g.

From chromatography on silica gel plates, using as solvent chloroform/methanol/ammonia 2.5N 55:45:10 and chloroform/methanol/CaCl$_2$ at 0.3% 55:45:10 and determined with resorcinol reagent, the product proves to be unitary and free from $G_{M1}$ and to have Rf of 0.02 and 0.06 respectively (Rf of $G_{M1}$, 0.45 and 0.65 respectively).

EXAMPLE 30

Maleate of 3-dimethylaminopropyl-1-amide of the ganglioside $G_{M1}$ 5 g of 3-dimethylaminopropyl-1-amide of the ganglioside $G_{M1}$ obtained, for example, as in the previous Example are dissolved in 100 ml of chloroform/methanol 1:1 and 400 mg (3.44 mM) of maleic acid are added to the solution.

After an hour of agitation at room temperature, the solution is evaporated in vacuum and the residue is gathered in 25 ml of chloroform/methanol 1:1 and the product precipitated in 200 ml of acetone. Yield in maleate of 3-dimethylaminopropyl-1-amide, 5.2 g.

EXAMPLE 31

Mixture of 3-dimethylaminopropyl-1-amides of of a ganglioside mixture 5 g of a mixture of the internal esters of gangliosides as described in Example 2 are dissolved in 20 ml of anhydrous pyridine and 1.51 g (14.8 mM) of 3-dimethylaminopropyl-1-amine are added to the solution and the mixture is agitated in anhydrous conditions for 24 hours at room temperature. Subsequent treatment is carried out as in Example 29. Yield of 3-dimethylaminopropyl-1-amide of the purified ganglioside mixture is 5.1 g.

Chromatography on silica gel plates, carried out as in Example 29 gives the following Rf values: 0.01–0.05 and 0.01–0.10 respectively (primary ganglioside mixture, Rf 0.15–0.70 and 0.20–0.70 respectively).

EXAMPLE 32

Maleate of the mixture of 3-dimethylaminopropyl-1-amides of ganglioside mixture 5 g of the mixture of 3-dimethylaminopropyl-1-amides of the ganglioside mixture, prepared as in the previous Example, are dissolved in 100 ml of chloroform/methanol 1:1 and 697 mg (6 mM) of maleic acid are added to the solution. After an hour of reaction, under agitation and at room temperature, the solution is evaporated in vacuum until dry and the residue is gathered with 25 ml of chloroform/methanol 1:1 and the product precipitated in 200 ml of acetone. Yield in maleic salt, 5.3 g.

EXAMPLE 33

Dimethylaminoethylamide of the ganglioside $G_{M1}$ 5 g of the internal ester of ganglioside $G_{M1}$ (3.27 mM) are dissolved in 50 ml of an anhydrous solution of chloroform/isopropanol 1:1 and then 537 mg (6.5 mM) of dimethylaminoethylamine are added.

The solution is agitated in anhydrous conditions for 24 hours at room temperature. Isolation and purification of the raw product thus obtained are effected as in Example 31, giving a yield of 4.9 g.

The product, chromatographed in the conditions described in the previous Example proves to be unitary and to have Rf of 0.11 and 0.14 respectively. IR spectroscopy shows no band at 1750 cm$^{-1}$.

EXAMPLE 34

Maleate of dimethylaminoethylamide of the ganglioside $G_{M1}$ 5 g of dimethylaminoethylamide of the ganglioside $G_{M1}$, obtained as described in the previous Example, are dissolved in 100 ml of chloroform/methanol 1:1 and 400 mg (3.44 mM) of maleic acid are added to the solution. After an hour at room temperature under agitation, the solution is evaporated in vacuum and the residue is gathered with 25 ml of chloroform/methanol 1:1 and the product precipitated in 200 ml of acetone. Yield: 5.2 g.

EXAMPLE 35

Mixture of dimethylaminoethylamides of a ganglioside mixture 5 g of a mixture of internal esters of a ganglioside mixture as described in Example 2, are dissolved in 50 ml of an anhydrous solution of chloroform/isopropanol 1:1 and 955 mg (0.8 mM) of dimethylaminoethylamine are added to the solution. The solution is kept at room temperature under agitation in anhydrous conditions for 24 hours.

Subsequent isolation and purification of the raw product are effected as described in Example 33. Chromatography on silica gel plates, carried out as in Example 33, gives Rf values of 0.01–0.14 and 0.01–0.16 respectively (original ganglioside mixture, 0.15–0.70 and 0.20–0.70 respectively). IR spectroscopy shows no ester band at 1750 cm$^{-1}$.

EXAMPLE 36

Maleate of the mixture of dimethylaminoethylamides of the ganglioside mixture 5 g of the mixture of dimethylaminoethylamides of the gangliosides described in the previous Example are dissolved in 100 ml of chloroform/methanol 1:1 and 697 mg (6 mM) of maleic acid are added to the solution.

After one hour, during which the solution is agitated at room temperature, the mixture is evaporated in vacuum until dry and the residue is gathered in 25 ml of chloroform/methanol 1:1 and the product precipitated with 200 ml of acetone. Yield: 5.3 g of the maleate.

EXAMPLE 37

Ethanolamide of the ganglioside $G_{M1}$ 5 g of the internal ester of the ganglioside $G_{M1}$ (3.27 mM) are dissolved in 50 ml of an anhydrous solution of chloroform/isopropanol 1:1 and 397.2 mg (6.5 mM) of ethanolamine are added to the solution. The mixture is kept in anhydrous conditions under agitation at room temperature.

Isolation and purification of the reaction product are carried out as in Example 33, giving 4.9 g of pure product.

Chromatography on silica gel plates with chloroform/methanol/ammonia 4N 55:45:10 and chloroform/methanol/CaCl$_2$ 0.3% 60:35:8 and determined with resorcinol reagent shows the product to be unitary and free from $G_{M1}$, with Rf of 0.12 and 0.49 respectively.

EXAMPLE 38

Mixture of ethanolamides of a ganglioside mixture

This mixture is prepared with 5 g of the mixture of internal esters of the ganglioside mixture described in Example 2, dissolved in 20 ml of anhydrous pyridine, and with 671 mg (10.8 mM) of ethanolamine. The mixture is agitated for 24 hours at room temperature.

Isolation of the raw product of the reaction, and its purification are carried out as in the previous Example, giving a yield of 5.2 g.

Chromatography on silica gel plates, carried out as in Example 33, shows Rf values of 0.09–0.56 and 0.25–0.55 respectively. IR spectroscopy did not show any typical ester band.

EXAMPLE 39

6-hydroxyhexyl-1-amide of the ganglioside $G_{M1}$ 5 g of internal ester of the ganglioside $G_{M1}$ (3.27 mM) are dissolved in 20 ml of anhydrous pyridine, and 762 mg (6.5 mM) of 6-hydroxyhexyl-1-amine. It is left to react under agitation for 24 hours at room temperature in anhydrous conditions. Isolation of the raw product of the reaction is carried out as in Example 28. Hydrolysis of the residue ester groups and dialysis are also carried out as in Example 12 and the purified product is precipitated with acetone as in the previous Examples. Yield: 4.3 g.

Chromatography on silica gel plates, using as solvents chloroform/methanol/ammonia 2.5N 60:40:9 and chloroform/methanol/CaCl$_2$ at 0.3% 60:35:8 and determined with resorcinol reagent, showed the product to be unitary and free from $G_{M1}$, with Rf of 0.40 and 0.80 respectively (Rf of $G_{M1}$, 0.42 and 0.40 respectively).

EXAMPLE 40

Peracetylated derivative of the ganglioside $G_{M1}$ 5 g of the sodium salt (3.19 mM) of the ganglioside $G_{M1}$ are dissolved in 50 ml of anhydrous pyridine and 25 ml of freshly distilled acetic anhydride are added to the solution at 25° C.

The solution is then kep in agitation for 72 hours at room temperature. At the end of the reaction, the solution is evaporated in vacuum until dry and the residue is partitioned with 100 ml of ice cold water and 200 ml of ethyl acetate.

The ethyl acetate is then washed with cold HCl 1.0M, with water and solutions of NaHCO$_3$ 1.0M. The organic layers are then anhydrified with sodium sulphate, evaporated in vacuum and the residue is purified by preparative column chromatography on silica gel using a mixture of dichloromethane/ethyl acetate/isopropanol 70:30:7 as eluent solvent. The pure fractions are mixed. Evaporated until dry, redissolved in 20 ml of ethyl acetate and the product precipitated in 100 ml of normal hexane.

Chromatography on silica gel plates, using dichloromethane/ethyl acetate/methanol 70:30:10 and ethyl acetate/isopropanol 95:5 and determined with Ehrlich reagent, shows the product to be unitary with Rf of 0.47 and 0.28 respectively.

EXAMPLE 41

Peracetylate derivative of a gnaglioside mixture 5 g of the ganglioside mixture described in Example 2 in the form of their sodium salts, are dissolved in 25 ml of anhydrous pyridine and 25 ml of acetic anhydride are added to the solution. The mixture is kept under agitation for 72 hours at room temperature. At the end of the reaction the solution is evaporated in vacuum until dry and the residue is divided between 100 ml of ice cold water and 200 ml of ethyl acetate, the ethyl acetate is washed with cold HCl 1.0N, with water and with a solution of $NaHCO_3$ 1.0M.

The organic layers are then anhydrified with sodium sulphate, evaporated in vacuum and the residue gathered in 20 ml of ethyl acetate and the product precipitated in 100 ml of normal hexane. Yield: 4.4 g.

Chromatography carried out as in the previous Example gives the mixture an Rf of 0.01–0.46 and 0.01–0.36 respectively.

EXAMPLE 42

Peracetylated derivative of the methyl ester of the ganglioside $G_{M1}$ 5 g (3.17 mM) of the methyl ester of the ganglioside $G_{M1}$ are dissolved in 50 ml of anhydrous pyridine and at 25° C., 25 ml of freshly distilled acetic anhydride are added to the solution and the mixture is kept in agitation for 72 hours at room temperature. At the end of the reaction the solution is evaporated in vacuum and the residue divided between 100 ml of ice cold water and 200 ml of ethyl acetate. The ethyl acetate is washed with cold HCl 1.0M, with water and with a solution of $NaHCO_3$ 1M. The organic layers are anhydrified with sodium sulphate, evaporated in vacuum and the residue purified by preparative chromatography on silica gel column, using as solvent a mixture of dichloromethane/ethyl acetate/isopropanol 70:30:45.

The pure fractions are mixed, evaporated, redissolved in 20 ml of ethyl ether and precipitated in 100 ml of normal hexane. Yield 4.5 g of peracetylated derivative of the methyl ester of $G_{M1}$ ganglioside. Chromatography on silica gel plates with dichloromethane/ethyl acetate/methanol 70:30:10 and ethyl acetate/isopropanol 95:5 and determined with Ehrlich reagent shows the product to be unitary with Rf of 0.47 and 0.28 respectively.

EXAMPLE 43

Peracetylated derivative of the mixture of methyl esters of a ganglioside mixture 5 g of the mixture of methyl esters of the ganglioside mixture described in Example 2 (see also Example 3) are acetylated as described in Example 40. Purification of the product of the acetylation is also carried out as in Example 40, giving a yield of 5.4 g of the peracetylated derivative of the methyl ester mixture of Example 3.

Chromatography carried out as in the previous Example shows Rf in the range of 0.23–0.54 and 0.01–0.52.

EXAMPLE 44

Peracetylated derivative of the amide of the ganglioside $G_{M1}$

Starting with 5 g (3.20 mM) of the amide of $G_{M1}$ ganglioside in 50 ml of anhydrous pyridine the acetylated derivative is prepared as in Example 42. Purification is carried out as in Example 41, using, however, for the chromatography, dichloromethane/isopropanol 95:5 as solvent. Yield: 4.4 g of pure peracetylated derivative of the amide of $G_{M1}$ ganglioside.

The product proves to be unitary when chromatographed as in the previous Example with Rf of 0.43 and 0.48 respectively.

EXAMPLE 45

Peracetylated derivative of the amide mixture of a ganglioside mixture 5 g of the mixture of ganglioside amides described in Example 15 dissolved in 50 ml of anhydrous pyridine are acetylated with 25 ml of acetic anhydride as in the previous Example, Purification is carried out as in Example 42, giving 4.9 g of peracetylated derivative of the ganglioside amides of Example 15.

Chromatographed in the same conditions as in the previous Example, the compound has Rf of 0.11–0.45 and 0.01–0.50 respectively.

EXAMPLE 46

Phenylethyl ester of the ganglioside $G_{M1}$

The phenylethyl ester of $GM_1$ is prepared and isolated in the same manner as for the methyl ester in Example 1, using however phenethyl alcohol and sodium phenylethylate in the place of methyl alcohol and sodium methylate and heating on a water bath, and using the same molar quantities of internal ester and sodium phenylethylate as in Example 1. Washing of the Dowex resin is effected with phenylethyl alcohol and the residue obtained by evaporation of the filtered substance is dissolved in 50 ml of methylenechloride/phenethyl alcohol 1:1. The yield in raw product is 5.1 g. Purification is also carried out as in Example 1. Yield of the purified phenylethyl ester of $GM_1$ ganglioside. 4.3 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.90 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 47

Mixture of phenylethyl esters of a mixture of ganglioside

The mixture of phenylethyl esters is prepared and isolated in the same way as for the mixture of methyl esters of Example 2, using however phenethyl alcohol and sodium phenylethylate instead of methyl alcohol and sodium methylate and heating on a water bath, and using 5 g of internal ester mixture and 844.8 mg (5.86 mM) of sodium phenylethylate. Washing of the Dowex resin is carried out with phenylethyl alcohol and the residue obtained by evaporation of the filtered substance is dissolved in 50 ml of chloroform/phenylethyl alcohol 1:1. The yield in raw product is 5.3 g. Purification is also carried out as in Example 3. The yield in purified ester mixture: 4.4 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.65–0.887 (ganglioside mixture 0.2–0.60). Complete transesterification is demonstrated in the same way as described in Example 2.

EXAMPLE 48

2-Cyclohexylethyl ester of the ganglioside $GM_1$

The 2-cyclohexylethyl ester of $GM_1$ is prepared and isolated in the same manner as for the methyl ester in Example 1, using however 2-cyclohexylethanol and sodium 2-cyclohexyethylate in the place of methyl alcohol and sodium methylate and heating on a water bath, and using the same molar quantities of internal ester and sodium 2-cyclohexylethylate as in Example 1. Washing of the Dowex resin is effected with 2-cyclohexylethyl alcohol and the residue obtained by evaporation of the filtered substance is dissolved in 50 ml of methylenechloride/2-cyclohexylethanol 1:1. The yield in raw product is 5.1 g. Purification is also carried out as in Example 1. Yield of the purified 2-cyclohexylethyl ester of $GM_1$ ganglioside: 4.3 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.92 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 49

Mixture of 2-cyclohexylethyl esters of a mixture of gangliosides

The mixture of 2-cyclohexylethyl esters is prepared and isolated in the same way as for the mixture of methyl esters of Example 2, using however 2-cyclohexylethanol and sodium 2-cyclohexylethylate instead of methyl alcohol and sodium methylate and heating on a water bath, and using 5 g of internal ester mixture and 880.3 mg (5.86 mM) of sodium 2-cyclohexylethylate. Washing of the Dowex resin is carried out with 2-cyclohexylethyl alcohol and the residue obtained by evaporation of the filtered substance is dissolved in 50 ml of chloroform/ethanol 1:1. The yield in raw product is 5.3 g. Purification is also carried out as in Example 3. The yield in purified ester mixture: 4.3 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.67–0.90 (ganglioside mixture 0.20–0.60). Complete transesterification is demonstrated in the same way as described in Example 2.

EXAMPLE 50

Menthyl ester of the ganglioside $GM_1$

The menthyl ester of $GM_1$ is prepared and isolated in the same manner as for the methyl ester in Example 1, using however menthol and sodium menthylate in the place of methyl alcohol and sodium methylate and heating on a water bath, and using the same molar quantities of internal ester and sodium menthylate as in Example 1. Washing of the Dowex resin is effected with menthyl alcohol/methylene chloride 1:1 and the residue obtained by evaporation of the filtered substance is dissolved in 50 ml of methylenechloride/menthol 1:1. The yield in raw product is 3.9 g. Purification is also carried out as in Example 1. Yield of the purified menthyl ester of $GM_1$ ganglioside: 4.2 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.93 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 51

Mixture of menthyl esters of a mixture of gangliosides

The mixture of menthyl esters is prepared and isolated in the same way as for the mixture of methyl esters of Example 2, using however menthol and sodium menthylate instead of methyl alcohol and sodium methylate and heating on a water bath, and using 5 g of internal ester mixture and 1038.8 mg (5.86 mM) of sodium menthylate. Washing of the Dowex resin is carried out with menthyl alcohol/methylene chloride 1:1 and the residue obtained by evaporation of the filtered substance is dissolved in 50 ml of chloroform/ethanol 1:1. The yield in raw product is 5.2 g. Purification is also carried out as in Example 3. The yield in purified ester mixture: 4.3 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.70–0.93 (ganglioside mixture 0.20–0.60). Complete transesterification is demonstrated in the same way as described in Example 2.

EXAMPLE 52

Tetrahydrofurfuryl ester of the ganglioside $GM_1$

The tetrahydrofurfuryl ester of $GM_1$ is prepared and isolated in the same manner as for the methyl ester in Example 1, using however, tetrahydrofurfuryl and sodium tetrahydrofurylate in the place of methyl alcohol and sodium methylate and heating on a water bath, and using the same molar quantities of internal ester and sodium tetrahydrofurfurylate as in Example 1. Washing of the Dowex resin is effected with tetrahydrofurfuryl alcohol and the residue obtained by evaporation of the filtered substance is dissolved in 50 ml of methylene chloride/tetrahydrofurfuryl alcohol 1:1. The yield in raw product is 5.0 g. Purification is also carried out as in Example 1. Yield of the purified tetrahydrofurfuryl ester of $GM_1$ ganglioside: 4.2 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.72 and the absence of $GM_1$ ganglioside and its internal ester (Rf 0.65 and 0.75, respectively). Hydrolysis with $Na_2CO_2$ as described in Example 1 produces the ganglioside $GM_1$.

EXAMPLE 53

Mixture of tetrahydrofurfuryl esters of a mixture of gangliosides

The mixture of tetrahydrofurfuryl esters is prepared and isolated in the same way as for the mixture of methyl esters of Example 2, using however tetrahydrofurfuryl alcohol and sodium tetrahydrofurfurylate instead of methyl alcohol and sodium methylate and heating on a water bath, and using 5 g of internal ester mixture and 727.5 mg (5.86 mM) of sodium tetrahydrofurfurylate. Washing of the Dowex resin is carried out with tetrahydrofurfuryl alcohol and the residue obtained by evaporation of the filtered substance is dissolved in 50 ml of chloroform/ethanol 1:1. The yield in raw product is 5.2 g. Purification is also carried out as in Example 2. The yield in purified ester mixture: 4.2 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.45–0.68 (ganglioside mixture 0.20–0.60). Complete transesterification is demonstrated in the same way as described in Example 2.

EXAMPLE 54

Tetrahydro-2H-pyran-4-yl ester of the ganglioside $GM_1$

The tetrahydro-2H-pyran-4-yl ester of $GM_1$ is prepared and isolated in the same manner as for the methyl ester in Example 1, using however tetrahydro-2H-pyran-4-ol and sodium tetrahydro-2H-pyran-4-ylate in the place of methyl alcohol and sodium methylate and heating on a water bath, and using the same molar quantities of internal ester and sodium tetrahydro-2H-pyran-4-ylate as in Example 1. Washing of the Dowex resin is effected with tetrahydro-2H-pyran-4-ol and the residue obtained by evaporation of the filtered substance is dissolved in 50 ml of methylene chloride/tetrahydro-2H-pyran-4-ol 1:1. The yield in raw product is 5.1 g. Purification is also carried out as in Example 1. Yield of the purified tetrahydro-2H-pyran-4-yl ester of $GM_1$ ganglioside: 4.3 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.73 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 55

Mixture of tetrahydro-2H-pyran-4-yl esters of a mixture of gangliosides

The mixture of tetrahydro-2H-pyran-4-yl esters is prepared and isolated in the same way as for the mixture of methyl esters of Example 2, using however tetrahydro-2H-pyran-4-ol and sodium tetrahydro-2H-pyran-4-ylate instead of methyl alcohol and sodium methylate and heating on a water bath, and using 5 g of internal ester mixture and 727.5 mg (5.86 mM) of sodium tetrahydro-2H-pyran-4-ylate. Washing of the Dowex resin is carried out with tetrahydro-2H-pyran-4-yl alcohol and the residue obtained by evaporation of the filtered substance is dissolved in 50 ml of chloroform/ethanol 1:1. The yield in raw product is 5.3 g. Purification is also carried out as in Example 3. The yield in raw product is 5.3 g. Purification is also carried out as in Example 3. The yield in purified ester mixture: 4.5 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.48–0.72 (ganglioside mixture 0.20–0.60). Complete transesterification is demonstrated in the same way as described in Example 2.

EXAMPLE 56

1-Heptyl ester of the ganglioside $GM_1$

The 1-heptyl ester of $GM_1$ is prepared and isolated in the same manner as for the methyl ester in Example 1, using however 1-heptanol and sodium 1-heptylate in the place of methyl alcohol and sodium methylate and heating on a water bath, and using the same molar quantities of internal ester and sodium 1-heptylate as in Example 1. Washing of the Dowex resin is effected with 1-heptyl alcohol and the residue obtained by evaporation of the filtered substance is dissolved in 50 ml of methylene chloride/1-heptanol 1:1. The yield in raw product is 3.9 g. Purification is also carried out as in Example 1. Yield of the purified 1-heptyl ester of $GM_1$ ganglioside: 4.3 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.89 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 57

Mixture of 1-heptyl esters of a mixture of gangliosides

The mixture of 1-heptyl esters is prepared and isolated in the same way as for the mixture of methyl esters of Example 2, using however 1-heptanol and sodium 1-heptylate instead of methyl alcohol and sodium methylate and heating on a water bath, and using 5 g of internal ester mixture and 809.8 mg (5.86 mM) of sodium 1-heptylate. Washing of the Dowex resin is carried out with 1-heptyl alcohol and the residue obtained by evaporation of the filtered substance is dissolved in 50 ml of chloroform/ethanol 1:1. The yield in raw product is 5.2 g. Purification is also carried out as in Example 2. The yield in raw product is 5.2 g. Purification is also carried out as in Example 2. The yield in purified ester mixture: 4.3 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.68–0.90 (ganglioside mixture 0.20–0.60). Complete transesterification is demonstrated in the same way as described in Example 2.

EXAMPLE 58

2-methyl-1-pentyl ester of the ganglioside $GM_1$

The 2-methyl-1-pentyl ester of $GM_1$ is prepared and isolated in the same manner as for the methyl ester in Example 1, using however 2-methyl-1-pentanol and sodium 2-methyl-1-pentylate in the plate of methyl alcohol and sodium methylate and heating on a water bath, and using the same molar quantities of internal ester and sodium 2-methyl-1-pentylate as in Example 1. Washing of the Dowex resin is effected with 2-methyl-1-pentyl alcohol and the residue obtained by evaporation of the filtered substance is dissolved in 50 ml of methylene chloride/2-methyl-1-pentanol 1:1. The yield in raw product is 5.1 g. Purification is also carried out as in Example 1. Yield of the purified 2-methyl-1-pentyl ester of $GM_1$ ganglioside: 4.4 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.90 and the absence of $GM_1$ ganglioside and its internal ester (Rf 0.65 and 0.75, respectively. Hydrolysis with $Na_2CO_3$ as described in Example 1 produces the ganglioside $GM_1$.

EXAMPLE 59

Mixture of 2-methyl-1-pentyl esters of a mixture of gangliosides

The mixture of 2-methyl-1-pentyl esters is prepared and isolated in the same way as for the mixture of methyl esters of Example 2, using however 2-methyl-1-pentanol and sodium 2-methyl-1-pentylate instead of methyl alcohol and sodium methylate and heating on a water bath, and using 5 g of internal ester mixture and 727.7 mg (5.86 mM) of sodium 2-methyl-1-pentylate. Washing of the Dowex resin is carried out with 2-methyl-1-pentyl alcohol and the residue obtained by evaporation of the filtered substance is dissolved in 50 ml of chloroform/ethanol 1:1. The yield in raw product is 5.3 g. Purification is also carried out as in Example 2. The yield in purified ester mixture: 4.4 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetraammonium 1M 55:45:10 and determined with Ehrlich reagent, the product shows an Rf of 0.70-0.93 (ganglioside mixture 0.20-0.60). Complete transesterification is demonstrated in the same way as described in Example 2.

EXAMPLE 60

3-methyl-2-pentyl ester of the ganglioside $GM_1$

The 3-methyl-2-pentyl ester of $GM_1$ is prepared and isolated in the same manner as for the methyl ester in Example 1, using however 3-methyl-2-pentanol and sodium 3-methyl-2-pentylate in the place of methyl alcohol and sodium methylate and heating on a water bath, and using the same molar quantities of internal ester and sodium 3-methyl-2-pentylate as in Example 1. Washing of the Dowex resin is effected with 3-methyl-2-pentyl alcohol and the residue obtained by evaporation of the filtered substance is dissolved in 50 ml of methylene chloride/3-methyl-2-pentanol 1:1. The yield in raw product is 5.1 g. Purification is also carried out as in Example 1. Yield of the purified 3-methyl-2-pentyl ester of $GM_1$ ganglioside: 4.2 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.92 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 61

Mixture of 3-methyl-2-pentyl esters of a mixture of gangliosides

The mixture of 3-methyl-2-pentyl esters is prepared and isolated in the same way as for the mixture of methyl esters of Example 2, using however 3-methyl-2-pentanol and and sodium 3-methyl-2-pentylate instead of methyl alcohol and sodium methylate and heating on a water bath, and using 5 g of internal ester mixture and 727.7 mg (5.86 mM) of sodium 3-methyl-2-pentylate. Washing of the Dowex resin is carried out with 3-methyl-2-pentyl alcohol and the residue obtained by evaporation of the filtered substance is dissolved in 50 ml of chloroform/ethanol 1:1. The yield in raw product is 5.3 g. Purification is also carried out as in Example 2. The yield in purified ester mixture: 4.4 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.72-0.95 (ganglioside mixture 0.20-0.60). Complete transesterification is demonstrated in the same way as described in Example 2.

EXAMPLE 62

3-methoxyethyl ester of the ganglioside $GM_1$

The 2-methoxyethyl ester of $GM_1$ is prepared and isolated in the same manner as for the methyl ester in Example 1, using however 2-methoxyethanol and sodium 2-methoxyethylate in the place of methyl alcohol and sodium methylate and heating on a water bath, and using the same molar quantities of internal ester and sodium 2-methoxyethylate as in Example 1. Washing of the Dowex resin is effected with 2-methoxyethyl alcohol and the residue obtained by evaporation of the filtered substance is dissolved in 50 ml of methylene chloride/2-methoxyethanol 1:1. The yield in raw product is 4.9 g. Purification is also carried out as in Example 1. Yield of the purified 2-methoxyethyl ester of $GM_1$ ganglioside: 4.3

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.77 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 63

Mixture of 2-methoxyethyl esters of a mixture of gangliosides

The mixture of 2-methoxyethyl esters is prepared and isolated in the same way as for the mixture of methyl esters of Example 2, using however 2-methoxyethanol and sodium 2-methoxyethylate instead of methyl alcohol and sodium methylate and heating on a water bath, and using 5 g of internal ester mixture and 574.9 mg (5.86 mM) of sodium 2-methoxyethylate. Washing of the Dowex resin is carried out with 2-methoxyethyl alcohol and the residue obtained by evaporation of the filtered substance is dissolved in 50 ml of chloroform/ethanol 1:1. The yield in raw product is 5.2 g. Purification is also carried out as in Example 3. The yield in purified ester mixture: 4.3 g. IR spectroscopy carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.51-0.78 (ganglioside mixture 0.20-0.60). Complete transesterification is demonstrated in the same way as described in Example 2.

EXAMPLE 64

1-methoxy-2-propyl ester of the ganglioside $GM_1$

The 1-methoxy-2-propyl ester of $GM_1$ is prepared and isolated in the same manner as for the methyl ester in Example 1, using however 1-methoxy-2-propanol and sodium 1-methoxy-2-propylate in the place of methyl alcohol and sodium methylate and heating on a water bath, and using the same molar quantities of internal ester and sodium 1-methoxy-2-propylate as in Example 1. Washing the Dowex resin is effected with 1-methoxy-2-propyl alcohol and the residue obtained by evaporation of the filtered substance is dissolved in 50 ml of methylene chloride/1-methoxy-2-propanol 1:1. The yield in raw product is 4.9 g. Purification is also carried out in Example 1. Yield of the purified 1-methoxy-2-propyl ester of $GM_1$ ganglioside: 4.2 g.

IR spectroscopic examination on KBr pellets shows the typical band of the ester at 1750 cm$^{-1}$. Chromatographic analysis of the product carried out in the same way as in Example 1 shows the presence of a unitary compound with an Rf of 0.81 and the absence of $GM_1$ ganglioside and its internal ester (Rf 0.65 and 0.75, respectively). Hydrolysis with $Na_2CO_3$ as described in Example 1 produces the ganglioside $GM_1$.

EXAMPLE 65

Mixture of 1-methoxy-2-propyl esters of a mixture of gangliosides

The mixture of 1-methoxy-2-propyl esters is prepared and isolated in the same way as for the mixture of methyl esters of Example 2, using however 1-methoxy-2-propanol and sodium 1-methoxy-2-propylate instead of methyl alcohol and sodium methylate and heating on a water bath, and using 5 g of internal ester mixture and 657.0 mg (5.86 mM) of sodium 1-methoxy-2-propylate. Washing of the Dowex resin is carried out with 1-methoxy-2-propyl alcohol and the residue obtained by evaporation of the filtered substance is dissolved in 50 ml of chloroform/ethanol 1:1. The yield in raw product is 5.2 g. Purification is also carried out as in Example 2. The yield in purified ester mixture: 4.3 g.

IR spectroscopy, carried out on KBr pellets, shows the typical band of the ester at 1750 cm$^{-1}$. When it is chromatographed on silica gel plates with a freshly prepared solution of chloroform/methanol/hydroxide of tetramethylammonium 1M 55:45:10 and determined with Ehrlich reagent, the product shows an Rf of 0.52-0.80 (ganglioside mixture 0.20-0.60). Complete transesterification is demonstrated in the same way as described in Example 2.

EXAMPLE 66

Cyclohexyl ester of the ganglioside $GM_1$ 5 g. of potassium salt (3.4 mM) of the ganglioside $GM_1$ are dissolved in 50 ml of DMSO and 661.5 mg (3.75 mM) of bromocyclohexane and 625 mg (3.75 mM) of KI are added to the solution. It is left to react for 48 hours at 25° C. At the end of the reaction the solution is partitioned with n-butanol/$H_2O$ 2:1 to eliminate the DMSO and the salts. The butanol solution is evaporated by drying and the residue is gathered in 50 ml of chloroform/methanol 1:1 and the product is precipitated with 250 ml of acetone. The raw product thus obtained (5.2 g) is then purified by preparative column chromatography on silica gel using as solvent a mixture of chloroform/methanol/water 60:35:8. The pure fractions are mixed, evaporated, redissolved in 15 ml of chloroform/isopropanol 1:1 and the product is precipitated with 75 ml of acetone. Pure cyclohexyl ester yield 4.4 g.

IR spectroscopy, carried out on KBr pellets, shows the typical ester bond at 1750 cm$^{-1}$. Chromatographed on silica gel plates with chloroform/methanol/$CaCl_2$ at 0.3% 60:40:9 and with chloroform/methanol/ammonia 2.5N 55:45:10 and determined with Ehrlich reagent, the product proves to be a uknitary compound with Rf of 0.70 and 0.58 respectively and to be free from starting ganglioside $GM_1$ (Rf 0.40 and 0.45 respectively). Treatment with a solution of $Na_2CO_3$ 0.1N at 60° for an hour causes the splitting of the ester bond, giving starting ganglioside $GM_1$.

EXAMPLE 67

Undecyl ester of the ganglioiside $GM_1$ 5 g. of potassium salt (3.14 mM) of the ganglioside $GM_1$ are dissolved in 50 ml of DMSO and 882.1 mg (3.75 mM) of 1-bromoundecane and 625 mg (3.75 mM) of KI are added to the solution. It is left to react for 48 hours at 25° C. At the end of the reaction the solution is partitioned with n-butanol/$H_2O$ 2:1 to eliminate the DMSO and the salts. The butanol solution is evaporated by drying and the residue is gathered in 50 ml of chloroform/methanol 1:1 and the product is precipitated with 250 ml of acetone. The raw product thus obtained (5.3 g) is then purified by preparative column chromatography on silica gel using as solvent a mixture of chloroform/methanol/water 60:35:8. The pure fractions are mixed, evaporated, redissolved in 15 ml of chloroform/isopropanol 1:1 and the product is precipitated with 75 ml of acetone. Pure undecyl ester yield 4.9 g.

IR spectroscopy, carried out on KBr pellets, shows the typical ester bond at 1750 cm$^{-1}$. Chromatographed on silica gel plates with chloroform/methanol/$CaCl_2$ at 0.3% 60:40:9 and with chloroform/methanol/ammonia 2.5N 55:45:10 and determined with Ehrlich reagent, the product proves to be a unitary compound with Rf of 0.68 and 0.56 respectively and to be free from starting ganglioside $GM_1$ (Rf 0.40 and 0.45 respectively). Treatment with a solution of $Na_2CO_3$ 0.1N at 60° for an hour causes the splitting of the ester bond, giving starting ganglioside $GM_1$.

EXAMPLE 68

1-hydroxy-undecan-11-yl ester of the ganglioside $GM_1$ 5 g of potassium salt (3.14 mM) of the ganglioside $GM_1$ are dissolved in 50 ml of DMSO and 0.42 mg (3.75 mM) of 11-bromo-1-undecanol and 625 mg (3.75 mM) of KI are added to the solution. It is left to react for 48 hours at 25° C. At the end of the reaction the solution is partitioned with n-butanol/$H_2O$ 2:1 to eliminate the DMSO and the salts. The butanol solution is evaporated by drying and the residue is gathered in 50 ml of chloroform/methanol 1:1 and the product is precipitated with 250 ml of acetone. The raw product thus obtained (5.3 g) is then purified by preparative column chromatography on silica gel using as solvent a mixture of chloroform/methanol/water 60:35:8. The pure fractions are mixed, evaporated, redissolved in 15 ml of chloroform, isopropanol 1:1 and the product is precipitated with 75 ml of acetone. Pure 11-hydroxy-undecan-11-yl ester yield 4.8 g.

IR spectroscopy, carried out on KBr pellets, shows the typical ester bond at 1750 $cm^{-1}$. Chromatographed on silica gel plates with chloroform/methanol/$CaCl_2$ at 0.3% 60:40:9 and with chloroform/methanol/ammonia 2.5N 55:45:10 and determineted with Ehrlich reagent, the product proves to be a unitary compound with Rf of 0.65 and 0.52 respectivley and to be free from starting ganglioside $GM_1$ (Rf 0.40 and 0.45 respectivley). Treatment with a solution of $Na_2CO_3$ 0.1N at 60° C. for an hour causes the splitting of the ester bond, giving the original ganglioside $GM_1$.

EXAMPLE 69

Byanobutyr-4-yl ester of the ganglioside $GM_1$ 5 g of potassium salt (3.14 mM) of the ganglioside $GM_1$ are dissolved in 50 ml of DMSO and 550 mg (3.75 mM) of 4-bromobutyronitrile and 625 mg (3.75 mM) of KI are added to the solution. It is left to react for 48 hours at 25° C. At the end of the reaction the solution is partitioned with n-butanol/$H_2O$ 2:1 to eliminate the DMSO and the salts. The butanol solution is evaporated by drying and the residue is gathered in 50 ml of chloroform/methanol 1:1 and the product is precipitated with 250 ml of acetone. The raw product thus obtained (5.1 g) is then purified by preparative column chromatography on silica gel, using as solvent a mixture of chloroform/methanol/water 60:35:8.

The pure fractions are mixed, evaporated, redissolved in 15 ml of chloroform/isopropanol 1:1 and the product is precipitated with 75 ml of acetone. Pure cyanobutyr-4-yl ester yield 4.6 g.

IR spectroscopy, carried out on KBr pellets, shows the typical ester bond at 1750 $cm^{-1}$. Chromatographed on silica gel plates with chloroform/methanol/$CaCl_2$ at 0.3% 60:40:9 and with chloroform/methanol/ammonio 2.5N 55:45:10 and determined with Ehrlich reagent, the product proves to be a unitary compound with Rf of 0.42 and 0.45 respectively and to be free starting ganglioside $GM_1$ (Rf 0.40 and 0.45 respectively). Treatment with a solution of $Na_2CO_3$ 0.1N at 60° C. for an hour causes the splitting of the ester bond, giving starting ganglioside $GM_1$.

EXAMPLE 70

Pyrrolidine amide of the ganglioside $GM_1$

This derivative is prepared from 5 g of internal ester of the ganglioside $GM_1$ (3.27 mM) and from 25 ml of pyrrolidine in the same way as in Example 16 and the same purification method is also followed. A yield of 5.1 g of pure pyrrolidine amide of the ganglioside $GM_1$ is obtained.

The IR spectroscopic data are the same as for the methylamide in Example 16 and chromatographic examination in the same conditions as in that Example proved the product to be unitary and free from $GM_1$ with Rf of 0.29 and 0.46 respectively (Rf of $GM_1$, 0.35 and 0.40 respectively).

EXAMPLE 71

Mixture of pyrrolidine amides of a ganglioside mixture

This derivative mixture is prepared with 5 g of the mixture of internal esters of gangliosides used in Example 17 and 25 ml of pyrrolidine in the same way as in Example 17, the same purification method is also used. A yield of 4.9 g of the mixture of pyrrolidine amides of a ganglioside mixture is obtained.

The Rf values determined by chromatography on silica gel plates with chloroform/methanol/ammonia 4N 55:45:10 and chloroform/methanol/$CaCl_2$ at 0.3% 60:35:8 and determined with resorcinol reagent proved to be 0.08–0.40 and 0.35–0.48 respectively (Rf of the original mixture of gangliosides 0.15–0.70 and 0.05–0.40 respectively).

EXAMPLE 72

Piperidine amide of the ganglioside $GM_1$

This derivative is prepared from 5 g of internal ester of the ganglioside $GM_1$ (3.27 mM) and from 25 ml of piperidinie in the same way as in Example 16 and the same purification method is also followed. A yield of 5.2 g of pure piperidine amide of the ganglioside $GM_1$ is obtained.

The IR spectroscopic data are the same as for the methylamide in Example 16 and chromatographic examination in the same condition as in that Example proved the product to be unitary and free from $GM_1$ with Rf of 0.30 and 0.50 respectively (Rf of $GM_1$, 0.35 and 0.40 respectively).

EXAMPLE 73

Mixture of piperidine amides of a ganglioside mixture

This derivative mixture is prepared with 5 g of the mixture of internal esters of gangliosides used in Example 17 and 25 ml of piperidine in the same way as in Example 17, the same purification method is also used. A yield of 5.1 g of the mixture of piperidine amides of a ganglioside mixture is obtained.

The Rf values determined by chromatography on silica gel plates with chloroform/methanol/ammonia 4N 55:45:10 and chloroform/methanol/$CaCl_2$ at 0.3% 60:35:8 and determined with resorcinol reagent proved to be 0.10–0.42 and 0.37–0.50 respectively (Rf of the original mixture of gangliosides 0.15–0.70 and 0.05–0.40 respectively).

EXAMPLE 74

Tetrahydrofurfuryl amide of the ganglioside GM$_1$

This derivative is prepared from 5 g of internal ester of the ganglioside GM$_1$ (3.27 mM) and from 25 Ml of tetrahydrofurfurylamine in the same way as in Example 16 and the same purification method is also followd. A yield of 5.3 g of pure tetrahydrofurfuryl amide of the ganglioside GM$_1$ is obtained.

The IR spectroscopic data are the same as for the methylamide in Example 16 and chromatographic examination in the same conditions as in that Example proved the product to be unitary and free from GM$_1$ with Rf of 0.33 and 0.52 respectively (Rf of GM$_1$, 0.35 and 0.40 respectively).

EXAMPLE 75

Mixture of tetrahydrofurfuryl amides of a ganglioside mixture

This derivative mixture is prepared with 5 g of the mixture of internal esters of gangliosides used in Example 17 and 25 ml of tetrahydrofurfurylamine in the same way as in Example 17, the same purification method is also used. A yield of 5.2 g of the mixture of tetrahydrofurfuryl amides of a ganglioside mixture is obtained.

The Rf values determined by chromatography on silica gel plates with chloroform/methanol/ammonia 4N 55:45:10 and chloroform/methanol/CaCl$_2$ at 0.3% 60:35:8 and determined with resorcinol reagent proved to be 0.12–0.45 and 0.40–0.57 respectively (Rf of the original mixture of gangliosides 0.15–0.70 and 0.05–0.40 respectively).

EXAMPLE 76

2-Methylpiperidine amide of the ganglioside GM$_1$

This derivative is prepared from 5 g of internal ester of the ganglioside GM$_1$ (3.27 mM) and from 25 ml of 2-methyl-piperidine amine in the same way as in Example 16 and the same purification method is also followed. A yield of 5.2 g of pure 2-methylpiperidine amide of the ganglioside GM$_1$ is obtained.

The IR spectroscopic data are the same as for the methylamide in Example 16 and chromatographic examination in the same conditions as in that Example proved the product to be unitary and free from GM$_1$ with Rf of 0.33 and 0.54 respectively (Rf of GM$_1$, 0.35 and 0.40 respectively).

EXAMPLE 77

Mixture of 2-methylpiperidine amides of a ganglioside mixture

This derivative mixture is prepared with 5 g of the mixture of internal esters of gangliosides used in Example 17 and 25 ml of 2-methylpiperidine in the same way as in Example 17 and 25 ml of 2-methylpiperidine in the same way as in Example 17, the same purification method is also used. A yield of 5.4 g of the mixture of 2-methylpiperidine amides of a ganglioside mixture is obtained.

The Rf values determined by chromatography on silica gel plates with chloroform/methanol/ammonia 4N 55:45:10 and chloroform/methanol/CaCl$_2$ at 0.3% 60:35:8 and determined with resorcinol reagent proved to be 0.14–0.46 and 0.39–0.59 respectively (Rf of the original mixture of gangliosides 0.15–0.70 and 0.05–0.40 respectively).

EXAMPLE 78

1-Methyl-piperazine amide of the ganglioside GM$_1$

This derivative is prepared from 5 g of internal ester of the ganglioside GM$_1$ (3.27 mM) and from 25 ml of 1-methylpiperazine in the same way as in Example 16 and the same purification method is also followed. A yield of 5.1 g of pure 1-methyl-piperazine amide of the ganglioside GM$_1$ is obtained. The IR spectroscopic data are the same as for the methylamide in Example 16 and chromatographic examination in the same conditions as in that Example proved the product to be unitary and free from GM$_1$ with Rf of 0.04 and 0.08 respectively (Rf of GM$_1$, 0.35 and 0.40 respectively).

EXAMPLE 79

Mixture of 1-methyl-piperazine amides of a ganglioside mixture

This derivative mixture is prepared with 5 g of the mixture of internal esters of gangliosides used in Examples 17 and 25 ml of 1-methyl-piperazine in the same way as in Example 17, the same purification method is also used. A yield of 5.5 g of the mixture of 1-methyl-piperazine amides of a ganglioside mixture is obtained.

The Rf values determined by chromatography on silica gel plates with chloroform/methanol/CaCl$_2$ at 0.3% 60:35:8 and determined with resorcinol reagent proved to be 0.01–0.06 and 0.01–0.12 respectively (Rf of the original mixture of gangliosides 0.15–0.70 and 0.05–0.40 respectively).

EXAMPLE 80

2-Phenylethyl amide of the ganglioside GM$_1$

This derivative is prepared from 5 g of internal ester of the ganglioside GM$_1$ (3.27 mM) and from 25 ml of 2-phenyl-ethyl amine in the same way as in Example 16 and the same purification method is also followed. A yield of 5.3 g of pure 2-phenylethyl amide of the ganglioside GM$_1$ is obtained.

The IR spectroscopic data are the same as for the methylamide in Example 16 and chromatographic examination in the same conditions as in that Example proved the product to be unitary and free from GM$_1$ with Rf of 0.33 and 0.73 respectively (Rf of GM$_1$, 0.35 and 0.40 respectively).

EXAMPLE 81

Mixture of 2-phenylethyl amides of a ganglioside mixture

This derivative mixture is prepared with 5 g of the mixture of internal esters of gangliosides used in Example 17 and 25 ml of 2-phenylethyl amine in the same way as in Example 17, the same purification method is also used. A yield of 5.5 g of the mixture of 2-phenylethyl amides of a ganglioside mixture is obtained.

The Rf values determined by chromatography on silica gel plates with chloroform/methanol/ammonia 4N 55:45:10 and chloroform/methanol/CaCl$_2$ at 0.3% 60:35:8 and determined with resorcinol reagent proved to be 0.12–0.44 and 0.60–0.78 respectively (Rf of the original mixture of gangliosides 0.15–0.70 and 0.05–0.40 respectively).

Pharmaceutical Preparations

As discussed above, one of the objects of the present invention resides in pharmaceutical preparations containing, as an active substance, one or more of the new ganglioside derivatives described above and, in particular; those derived from ganglioside groups A and B, as well as the specific ones listed previously. Furthermore, the pharmaceutical preparations of the present invention include esterified derivatives or amides and their acylated derivatives, including those already known and those novel derivatives described above. Particularly preferred are the methyl esters of gangliosides $G_{M1}$ and $G_{M3}$ and their peracylated derivatives, as well as the amide of ganglioside $G_{M3}$.

The pharmaceutical preparations of the invention can be preparations for oral, rectal, parenteral, local or intradermal use. They are therefore in solid or semisolid form, such as pills, tablets, gelatine covered capsules, capsules, suppositories or soft gelatine capsules. For parenteral use, it is possible to use those forms intended for intramuscular, subcutaneous or intradermal administration or intended for infusions or intravenous injections, and which may, therefore, be presented as solutions of the active compounds or as freeze-dried powders of the active compounds to be added to one or more pharmaceutically acceptable excipients or diluents, suitable for the above uses and having osmolarity which is compatible with physiological liquids. Preparations in the form of sprays, such as nasal sprays, creams or ointments for topical use of suitably prepared plasters for intradermal administration can be utilized for local application. The preparations of the invention can be administered to humans or animals. Preferably, the compositions should contain between 0.01% and 10% of the active component, for solutions, sprays, ointments and creams and between 1% and 100% and preferably between 5% and 50% of the active compound for the solid preparations. The dosage to be administered depends on medical indication, on the desired effect and on the chosen administration route. Examples 82–83 illustrate the pharmaceutical preparations according to the invention.

EXAMPLE 82

Pharmaceutical preparations in solution for injection

| Preparation No. 1 | |
|---|---|
| one 2 ml vial contains: | |
| active substance | mg 5 |
| sodium chloride | mg 16 |
| citrate buffer pH 6 in | q.b.a. ml 2 |
| water distilled pyrogen free | |

The active substance may be chosen from the group composed of the ganglioside derivatives described in any of Examples: 14, 15, 16, 17, 18, 19, 20, 21, 22, 23 and 24.

| Preparation No. 2 | |
|---|---|
| one 2 ml vial contains: | |
| active substance | mg 50 |
| sodium chloride | mg 16 |
| citrate buffer pH 6 in | q.b.a. ml 2 |
| water distilled pyrogen free | |

The active substance may be chosen from the group composed of the ganglioside derivatives described in any of Examples: 25, 26, 27, 28, 29, 30, 31, 32, 33, 34, 35, 36, 37, 38 and 39.

| Preparation No. 3 | |
|---|---|
| one 4 ml flacon contains: | |
| active substance | mg 100 |
| sodium chloride | mg 32 |
| citrate buffer pH 6 in | q.b.a. ml 4 |
| water distilled pyrogen free | |

The active substance may be chosen from the group composed of the ganglioside derivatives described in any of Examples: 20–39.

Preparations Nos. 1, 2 and 3 may be administered directly to animals or humans by one of the routes describes above. The compounds may also contain other active substantance.

EXAMPLE 83

Pharmaceutical compositions prepared in double flacons

The preparations illustrated in this Example are obtained with double flacons. The first flacon contains the active substance in the form of a freeze-dried powder in quantities which may vary between 10% and 90% in weight, together with a pharmaceutically acceptable excipient, with glycine or mannitol. The second flacon contains the solvent, such as a solution of sodium chloride and a citrate buffer.

The contents of the two flacons are mixed immediately before use and the freeze-dried powder of the active substance dissolves rapidly, giving an injectable solution. Flacons containing freeze-dried powder of the active substance are the preferable pharmaceutical form of the present invention.

| System No. 1 | |
|---|---|
| a. one freeze-dried 2 ml flacon contains: | |
| active substance | mg 5 |
| glycine | mg 30 b. |
| one 2 ml vial of solvent contains: | |
| sodium chloride | mg 16 |
| citrate buffer in pyrogen free water | q.b.a. ml 2 |

The active substance may be chosen from the group composed of the ganglioside derivatives described in any of Examples: 14, 15, 16, 17, 18, 19, 20, 21, 22, 23 and 24.

| System No. 2 | |
|---|---|
| a. one 3 ml freeze-dried vial contains: | |
| active substance | mg 5 |
| mannitol | mg 40 b. |
| one 2 ml vial of solvent contains: | |
| sodium chloride | mg 16 |
| citrate buffer in pyrogen free water | q.b.a. ml 2 |

The active substance may be chosen from the group composed of the ganglioside derivatives described in any of Examples 1, 2, 4, 5, 6, 7, 8, 9, 10, 11, 12 and 13.

| System No. 3 | |
| --- | --- |
| a. one freeze-dried 3 ml vial contains: | |
| active substance | mg 50 |
| glycine | mg 25 |
| b. one 3 ml vial of solvent contains: | |
| sodium chloride | mg 24 |
| citrate buffer in pyrogen free water | q.b.a. ml 3 |

The active substance may be chosen from the group of ganglioside derivatives described in any of Examples 14, 15, 16, 17, 21, 37, 38 and 39.

| System No. 4 | |
| --- | --- |
| a. one freeze-dried 3 ml vial contains: | |
| active substance | mg 50 |
| mannitol | mg 20 |
| b. one 3 ml vial of solvent contains: | |
| sodium chloride | mg 24 |
| citrate buffer in pyrogen free water | q.b.a. ml 3 |

The active substance may be chosen from the group of ganglioside derivatives described in any of Examples 10–13 and 66–67.

| System No. 5 | |
| --- | --- |
| a. one freeze-dried 5 ml vial contains: | |
| active substance | mg 150 |
| glycine | mg 50 |
| b. one 4 ml vial of solvent contains: | |
| sodium chloride | mg 32 |
| citrate buffer in pyrogen free water | q.b.a. ml 4 |

The active substance may be chosen from the group composed of the ganglioside derivatives described in any of Examples 14–39.

| System No. 6 | |
| --- | --- |
| a. one freeze-dried 5 ml flacon contains: | |
| active substance | mg 100 |
| mannitol | mg 40 |
| b. one 4 ml vial of solvent contains: | |
| sodium chloride | mg 32 |
| citrate buffer in pyrogen free water | q.b.a. ml 4 |

The active substance may be chosen from the group of ganglioside derivatives described in any of Examples 5–9.

| Sample No. 7 | |
| --- | --- |
| a. one 3 ml flacon contains: | |
| sterile micronized active substance | mg 40 |
| b. one 3 ml vial of solvent contains: | |
| Tween 80 | mg 10 |
| sodium chloride | mg 24 |
| phosphate buffer in pyrogen free water | q.b.a. ml 3 |

The active substance may be chosen from the group of ganglioside derivatives described in any of Examples 40–45.

| System No. 8 | |
| --- | --- |
| a. one 5 ml flacon contains: | |
| sterile micronized active substance | mg 100 |
| b. one 4 ml vial of solvent contains: | |
| Tween 80 | mg 15 |
| soya lecithin | mg 5 |
| sodium chloride | mg 36 |
| citrate buffer in pyrogen free water | q.b.a. ml 4 |

The active substance may be chosen from the group of ganglioside derivatives described in any of Examples 40–45.

Therapeutic Activity

All of the new ganglioside derivatives discussed above, and in particular those gangliosides of groups A and B and the above-listed specific compounds, comprise the active ingredients of the pharmaceutical preparations of the present invention. Furthermore, these pharmaceutical preparations may also contain some ganglioside derivatives of the type described above and already known in literature, such as the methyl ester of ganglioside $G_{M1}$ or its peracetylated derivative. The invention also includes the application of all these ganglioside derivatives, both new and already known, for therapeutic use.

As discussed above, the therapeutic action of gangliosides and some derivatives, such as those of the present invention, is due to a stimulation of the sprouting phenomena of the nervous cell, due to which it is possible to obtain a recovery of nervous conduction. For example, the in vivo administration of a ganglioside mixture obtained from bovine brain as described in Example 2 (GA mixture) provokes sprouting of the sciatic nerve in rats after crushing, and can, therefore, aid in recovery of electric activity of the nerve at the neuromuscular joint level.

Since neurite sprouting may be considered as a localized neuronal differentiation, the biochemical mechanisms by which ganglioside molecules produce this effect were studied on the basis of their effect on cellular differentiation, using cellular cultures, in vitro, of pheocromocytoma $PC_{12}$. The addition of gangliosides to nerve growth factor (NGF), which is an inducer of differentiation of $PC_{12}$ cells, in the $PC_{12}$ culture medium stimulates neuronal sprouting. This effect may be attributed to the incorporation of gangliosides in the neuronal membrane which induces a modification of its functional properties, that is to say, the enzymatic activities. Indeed, the incorporation of gangliosides in the neuronal membrane is able to stimulate activity of ($Na^+$, $K^+$)-ATPase. To emphasize the importance of the activation of this enzyme connected to the membrane, it should be remembered that some authors trace the survival and consequently the differentiation of neuronal cells in culture back to an activation of this enzyme by NGF. On the other hand, the key role played by this enzyme in electric activity is well known, as it is involved in the ionic mechanism subjected to the propagation of nervous impulses along the axonal membrane.

On the basis of the methods described above, determinations were made of the pharmacological activities expressed by neurite sprouting in the $PC_{12}$ cells for the new ganglioside derivatives according to the present invention. Results obtained with ($Na^+$, $K^+$) ATPase in vitro of some derivatives are also reported.

Effects of ganglioside derivatives on neurite sprouting in $PC_{12}$ cells

Materials and methods

The $PC_{12}$ cell line (derived from a subclone 1A) was supplied by Dr. P. Calissano (C.N.R. Laboratory of Cellular Biology-Rome).

The cells (100,000/plate) are kept at 37° C. in a Heraeus incubator (5% $CO_2$ and 95% humidified air) and resown on 60 mm Falcon Integrid plates on a collagene support in the presence of the following culture medium: 85% RPM 1640 (Gibco), 10% heat-inactivated equine serum, 5% fetal calf serum (Gibco), 50 U/ml penicillin and 25 mg/ml of streptomycine. The cells are then washed three times in a serum-free vehicle. After three washes, the cells are incubated in a serum-free vehicle with 50 ng/ml of NGF and with the ganglioside derivative according to the invention or with the ganglioside mixture used as a comparison at concentrations of $10^{-6}$M. The addition of the serum-free vehicle with NGF (50 ng/ml) has the effect of interrupting the proliferation of the cells, forming neurites and obtaining the differentiation as early as the third day. This effect is evaluated by counting the number of cells with neurites at the third day.

Results

The results are reported in the following Table 1 using as comparison values those obtained with ganglioside mixture obtained according to the procedure described in Example 2 and the single monosialoganglioside fraction $G_{M1}$.

TABLE 1

Effects of gangliosides and their derivatives according to the present invention, on neurite sprouting in $PC_{12}$ cells.

| Compound | Concentration | % of the no. of cells with neurites at 3rd day |
|---|---|---|
| Controls | $10^{-6}$ M | 21.5 |
| Ganglioside mixture GA (see Example 2) | " | 39.5 |
| Monosialoganglioside $G_{M1}$ | " | 34.8 |
| Methylic ester of GA | " | 32.8 |
| Methylic ester of $G_{M1}$ | " | 35.7 |
| Ethylic ester of GA | " | 34.9 |
| Ethylic ester of $G_{M1}$ | " | 37.1 |
| Isopropylic ester of GA | " | 37.3 |
| Isopropylic ester of $G_{M1}$ | " | 37.0 |
| Tertiarbutylic ester of GA | " | 29.5 |
| Tertiarbutylic ester of $G_{M1}$ | " | 32.3 |
| Benzylic ester of GA | " | 31.4 |
| Benzylic ester of $G_{M1}$ | " | 28.3 |
| Allylic ester of GA | " | 34.1 |
| Allylic ester of $G_{M1}$ | " | 31.5 |
| Etoxycarbonylmethylic ester of $G_{M1}$ | " | 27.3 |
| Amide of GA | " | 36.3 |
| Amide of $G_{M1}$ | " | 33.3 |
| Methylamide of GA | " | 40.0 |
| Ethylamide of GA | " | 35.0 |
| Ethylamide of $G_{M1}$ | " | 32.2 |
| Benzylamide of GA | " | 26.7 |
| Benzylamide of $G_{M1}$ | " | 30.8 |
| Isopropylamide of $G_{M1}$ | " | 31.4 |
| Dimethylamide of GA | " | 29.3 |
| Dimethylamide of $G_{M1}$ | " | 34.3 |
| Diethylamide of GA | " | 25.0 |
| Diethylamide of $G_{M1}$ | " | 28.5 |
| Ethylmethylamide of $G_{M1}$ | " | 35.3 |
| 3-dimethylaminopropyl-1-amide of GA | " | 32.9 |
| 3-dimethylaminopropyl-1-amide of $G_{M1}$ | " | 37.3 |
| Dimethylaminoethylamide of $G_{M1}$ | " | 34.8 |
| Ethanolamide of GA | " | 38.3 |
| Ethanolamide of $G_{M1}$ | " | 41.2 |

TABLE 1-continued

Effects of gangliosides and their derivatives according to the present invention, on neurite sprouting in $PC_{12}$ cells.

| Compound | Concentration | % of the no. of cells with neurites at 3rd day |
|---|---|---|
| 6-hydroxyhexyl-1-amide of $G_{M1}$ | " | 36.4 |
| Peracetylated GA mixture | " | 28.5 |
| Peracetylated $G_{M1}$ | " | 30.2 |
| Methylic ester of peracetylated GA | " | 33.6 |
| Methylic ester of peracetylated $G_{M1}$ | " | 29.4 |
| Amide of peracetylated GA | " | 25.3 |
| Amide of peracetylated $G_{M1}$ | " | 31.4 |

Effects of ganglioside derivatives on ($Na^+$, $K^+$) ATPase of the neuronal membrane Materials and methods a. Preparation of the raw mitochondrial fraction of rat brain (Fraction P2):

The procedure used in the preparation of $P_2$ fraction was taken from Morgan e coll., Biochem. Biophys. Acta 241, 37 (1971). (The various operations were carried out at 0° to 4° C.; the xg values are average centrifugal forces).

Adult male Sprague Dawley rats (supplied by Charles River) (body weight 150-175 g) were decapitated and their brains were immediately removed and washed in an ice cold isotonic solution. After excision of the cerebellum, the brains were homogenized by effecting 12 up and down movements in a motor-driven glass and Telfon homogenizer (declared radial clearance 0.25 mm; 800 r.p.m.) using 4 vol. of homogenizing solution (0.32M saccharose containing 1 mM potassium phosphate buffer and 0.1 nM of disodium EDTA, pH 7.27). The homogenized substance, filtered through four layers of fine gauze, was centrifuged at 1000 r.p.m. for 15 minutes. The resulting pellet was washed with the same initial volume of homogenizing solution and centrifuged as described above. The gathered supernatants were centrifuged at 17,500 r.p.m. for 25 minutes (these conditions of gravitational centrifugal force were used to obtain the maximum enrichment of nervous terminations in the fraction) and the pellet was washed four times in 9 volumes (each time) of homogenizing solution and centrifuged (17,500 r.p.m. for 25 minutes).

The final pellet, known as "$P_2$ fraction" contains as its principal component, whole mitochondria and nervous terminations. The final pellet was homogeneously resuspended with a suitable volume of homogenizing solution with a glass and Teflon homogenizer, and used immediately for the test. In order to avoid inconsistencies due to conservation of the material, fresh $P_2$ fractions were prepared before each use. The preparations of $P_2$ fractions had a ganglioside content of bound 33.9±2.8 (S.D.) n moles of sialic acid per mg of protein.

b. Activation of the ATPase enzyme:

ATPase activity was measured by spectrophotometry according to Wallick and coll. [J. Pharm. Exptl. Therap. 189, 434, (1974)]. The reaction mixture, unless otherwise indicated, is composed of: 50 mM of saccharose, 0.2 mM of disodium EDTA (brought to pH 7.4), 100 mM NaCl, 5 mM $MgCl_2$, 10 mM KCl, 2 mM of monopotassic salt of phospho(enol)pyruvate (PEP) (brought to pH 7.4), 3 mM ATP, 50 mM TRIS-HCl pH 7.4, 0.33 mM NADH, pyruvate-kinase (PK) (30 g/ml) and lactate dehydrogenase (LDH) (10 g/ml) in a final volume of 3 ml and with a final pH of 7.2. The reaction is begun with the addition of 50-75 µg (as a protein) of the $P_2$ fraction. The $(Na^+, K^+)$ATPase activity is determined by the difference between the total ATPase activity and the dependent ATPase $Mg^{2+}$ activity measured in the presence of $3 \times 10^{-5}$M of Ouabain. The time taken for each single test was 3-5 minutes. The ATPase activity was expressed as International Unit (I.U.) (µmoles hydrolized ATP/mg protein/min). The activity of the ganglioside derivatives (50 nM) was dosed by carrying out incubation with the neuronal membranes at 37° C. for two hours.

Results

The results of the comparative studies on ATPase activity are reported in Table 2.

TABLE 2

Effects of gangliosides and their derivatives on the $(Na^+, K^+)$ATPase of the neuronal membrane

| Product | Concentration | % increase in $(Na^+, K^+)$ ATPase activity |
|---|---|---|
| Controls | 50 | 100 |
| Ganglioside mixture GA | 50 | 142 |
| GA (see Example 2) | | |
| $G_{M1}$ | 50 | 133 |
| Methyl ester of GA | 50 | 128 |
| Amide of GA | 50 | 139 |
| Methyl ester of $G_{M1}$ | 50 | 132 |
| Amide of $G_{M1}$ | 50 | 128 |

It should be noted that the ganglioside derivatives of the present invention have a more prolonged action in time compared to gangliosides and are therefore useful as "retard" medicaments. This phenomenon is illustrated for example by the following experiments on the kinetics of absorption of ganglioside esters.

In vivo blood distribution of ganglioside derivatives

1. Preparation of labelled products

Labelled ganglioside is prepared as described by Suzuki et al. [J. Lipid Res. 13, 687–690 (1972)] and modified by Ghidoni et al. [Ital. J. Biochem. 23, 320–328 (1974)]. The ethyl and isopropyl esters are prepared by esterification of this labelled ganglioside. The specific radioactivity is measured both of the ganglioside and esters.

2. Treatment of the animals

Swiss mice obtained from Charles River (Calco), weighing about 20-25 g were treated by intravenous route with 10 µC of the products. 2-4-8-12-16 hours after administration, the animals were sacrificed by decapitation and their blood was gathered in heparinized flasks. The nonvolatile radioactivity was determined on blood samples by means of a Packard TRI-CARB scintillator and then identified with reference to $^3$H ganglioside and to the esters by TLC.

3. Results

After intravenous administration of tritiated ganglioside, the kinetic curve was biphasic, declining with a t/2 of about three hours followed by a slow elimination phase which remains constant until the sixteenth hour. With the ethyl and isopropyl ester of $G_{M1}$ ganglioside, the levels of product at first identified do not reach the maximum observed with the natural product, but with time they reach higher maximums and remain at these levels for longer. In this way there is an increase in the distribution volume and an increase in the time of maintenance of the therapeutic doses.

Due to the pharmacological properties described above, the ganglioside derivatives of the present invention may be used as drugs in various therapies for treatment of nervous system pathologies, in particular therapies of the peripheral nerves and those of the central nervous system.

The invention particularly regards the therapeutic use of the ganglioside derivatives which are specifically mentioned above, such as the groups of derivatives of gangliosides A and B and those specified in detail and the administration of all these derivatives at the doses hereafter reported. More particularly, these ganglioside derivatives may be used in therapy of peripheral nervous system pathologies of traumatic, compressive, generative, or toxic-infective origin, in which it is necessary to stimulate nervous regeneration and recovery of neuromuscular function and in pathologies of the central nervous system of traumatic, anoxic, degenerative or toxic-infective origin in which it is necessary to stimulate neuronal sprouting phenomena in order to obtain functional recovery. Due to their retard effect, the ganglioside derivatives of the present invention have a clear advantage over gangliosides themselves, which have until now been the drugs used in the cases reported above.

The dosages for administration will depend on the desired effect and on the chosen administration route. Administration is usually effected by intramuscular, subcutaneous, intravenous, intradermal or pulmonal route, preferably in a suitably buffered aqueous vehicle. The pharmaceutical form for conserving the substance may in this case be vials containing solutions of the derivative, possibly with other auxiliary ingredients, as described for the pharmaceutical preparations of the present invention. For therapeutic or possibly also prophylactic application by the above mentioned parenteral route, the dosage may vary preferably between 0.05 mg and 5 mg of active substance per Kg of body weight/die and especially between 0.05 mg and 2 mg per Kg of body weight/die.

Although the new therapeutic applications according to the invention are generally suitable for all pathologies connected with nervous stimulus conduction in the central and peripheral nervous systems, the following specific pathologies are of particular interest: retrobulbar optical neurities, paralysis of the oculomotor nerves, neuritis of the trigeminus, Bell's palsy and paralysis of the facial nerve, Garcin's syndrome, radiculitis, traumatic lesions of the peripheral nerves, diabetic and alcoholic polyneuritis, obstetric paralysis, paralytic sciatica, motoneuron diseases, myelopathic muscular amyotrophic-atrophic lateral sclerosis, progressive bulbar paralysis, severe myasthenia, Lambert Eaton syndrome, muscular dystrophy, deterioration of synaptic nervous transmission in the CNS and PNS, and impairments in consciousness such as confusional states, cerebral concusion, thrombosis, embolism.

What is claimed is:

1. A ganglioside derivative comprised of an oligosaccharide moiety formed by 1 to 5 monosaccharides, at least one sialic acid moiety and at least one ceramide moiety, the carboxyl groups of said sialic acid moieties being esterified with an alcohol, said alcohol being a substituted or unsubstituted alcohol selected from the group consisting of a $C_{1-12}$ aliphatic alcohol, a $C_{1-12}$ araliphatic alcohol with only one benzene ring, a $C_{1-12}$ heterocyclic alcohol with one heterocyclic ring containing a heteroatom selected from the group consisting of N, S and O, a $C_{1-14}$ alicyclic alcohol, and a $C_{1-14}$ aliphaticalicyclic alcohol containing only one cycloaliphatic ring, with the proviso that said ganglioside derivative is not the methyl ester of ganglioside $G_{M1}$ or $G_{M3}$.

2. A ganglioside derivative according to claim 1, wherein the hydroxyl groups of said ceramide moiety and said oligosaccharide moiety are acylated with a carboxylic acid, said carboxylic acid being a substituted or unsubstituted carboxylic acid selected from the group consisting of a $C_{1-10}$ aliphatic, $C_{1-10}$ aromatic, $C_{1-10}$ araliphatic, $C_{1-10}$ alicyclic and $C_{1-10}$ heterocyclic carboxylic acid.

3. A ganglioside derivative as in claim 1, wherein the oligosaccharide is formed of a maximum of 4 hexoses selected from the group consisting of glucose and galactose or of N-acetylhexoseamines selected from the group consisting of N-acetylglucosamine and N-acetylgalactosamine, there being present at least one hexose residue, and in which the oligosaccharide is unitary as to its chemical structure, and in which the ceramide residue derives from an aggregation of acylsphingosines which are either saturated or have one double bond and a chain of 16 to 22 carbon atoms, and in which the residues of the sialic acids derive from the group consisting of N-acetylneuraminic acid and N-glycolylneuraminic acid and of their corresponding acids acylated at one of the hydroxy groups.

4. A ganglioside derivative as in claim 2, wherein the oligosaccharide is formed of a maximum of 4 hexoses selected from the group consisting of glucose and galactose or of N-acetylhexoseamines selected from the group consisting of N-acetylglucosamine and N-acetylgalactosamine, there being present at least one hexose residue, and in which the oligosaccharide is unitary as to its chemical structure, and in which the ceramide residue derives from an aggregation of acylsphingosines which are either saturated or have one double bond and a chain of 16 to 22 carbon atoms, and in which the residues of the sialic acids derive from the group consisting of N-acetylneuraminic acid and N-glycolylneuraminic acid and of their corresponding acids acylated at one of the hydroxy groups.

5. A ganglioside as in claim 1, wherein the ceramide residue has sphingosine chains of 18 to 20 carbon atoms and acyl groups of 18 to 20 carbon atoms in length.

6. A ganglioside as in claim 2, wherein the ceramide residue has sphingosine chains of 18 to 20 carbon atoms and acyl groups of 18 to 20 carbon atoms in length.

7. A ganglioside derivative according to claim 1, wherein the basic gangliosides are selected from the group consisting of $G_{M1}$, $G_{D1a}$, $G_{D1b}$ and $G_{T1b}$.

8. A ganglioside derivative according to claim 2, wherein the basic gangliosides are selected from the group consisting of $G_{M1}$, $G_{D1a}$, $G_{D1b}$ and $G_{T1b}$.

9. A ganglioside derivative according to claim 1, wherein the carboxylic esterifying groups derive from aliphatic alcohols with a maximum of 12 carbon atoms, or from araliphatic alcohols with only one benzene ring.

10. A ganglioside derivative according to claim 2, wherein the carboxylic esterifying groups derive from aliphatic alcohols with a maximum of 12 carbon atoms, or from araliphatic alcohols with only one benzene ring.

11. A ganglioside derivative according to claim 1, selected from the group consisting of the ethyl, propyl, isopropyl, N-butyl, isobutyl, tertiary butyl, undecyl, hydroxydecyl, heptyl, 2-methyl-1-pentyl, allyl, ethoxycarbonylmethyl, methoxyethyl, 1-methoxy-2-propyl, benzyl, phenethyl, cyclohexyl, menthyl, tetrahydrofurfuryl, tetrahydropyranyl and cyanobutyryl esters of the gangliosides $G_{M1}$, $G_{D1b}$, $G_{D1a}$ and $G_{T1b}$ and the methyl esters of the gangliosides $G_{D1b}$, $G_{D1a}$ and $G_{T1b}$.

12. A ganglioside derivative according to claim 2, selected from the group consisting of the ethyl, propyl, isopropyl, N-butyl, isobutyl, tertiary butyl, undecyl, hydroxydecyl, heptyl, 2-methyl-1-pentyl, allyl, ethoxycarbonylmethyl, methoxyethyl, 1-methoxy-2-propyl, benzyl, phenethyl, cyclohexyl, menthyl, tetrahydrofurfuryl, tetrahydropyranyl and cyanobutyryl esters of the gangliosides $G_{M1}$, $G_{D1b}$, $G_{D1a}$ and $G_{T1b}$ and the methyl esters of the gangliosides $G_{D1b}$, $G_{D1a}$ and $G_{T1b}$.

13. A ganglioside derivative according to claim 1, selected from the group consisting of the peracetylates, perpropionylates, perbutyrrylates, maleinylates, and succinylates of said esters.

14. A ganglioside derivative according to claim 2, selected from the group consisting of the peracetylates, perpropionylates, perbutyrrylates, maleinylates, and succinylates of said esters.

15. A ganglioside derivative according to claim 1, selected from the group consisting of the peracetylates, perpropionylates, perbutyrrylates, maleinylates and succinylates of the gangliosides $G_{M1}$, $G_{D1b}$, $G_{D1a}$ and $G_{T1b}$.

16. A ganglioside derivative according to claim 2, selected from the group consisting of the peracetylates, perpropionylates, perbutyrrylates, maleinylates and succinylates of the gangliosides $G_{M1}$, $G_{D1b}$, $G_{D1a}$ and $G_{T1b}$.

17. A pharmaceutical composition comprising, as an active ingredient, an effective nerve pathology treatment amount of a ganglioside derivative according to claim 1.

18. A pharmaceutical composition comprising, as an active ingredient, an effective nerve pathology treatment amount of a ganglioside derivative according to claim 2.

19. A pharmaceutical composition comprising, as an active ingredient, an effective nerve pathology treatment amount of a ganglioside derivative according to claim 3.

20. A pharmaceutical composition comprising, as an active ingredient, an effective nerve pathology treatment amount of a ganglioside derivative according to claim 5.

21. A pharmaceutical composition comprising, as an active ingredient, an effective nerve pathology treatment amount of a ganglioside derivative according to claim 7.

22. A pharmaceutical composition comprising, as an active ingredient, an effective nerve pathology treatment amount of a ganglioside derivative according to claim 9.

23. A pharmaceutical composition comprising, as an active ingredient, an effective nerve pathology treatment amount of a ganglioside derivative according to claim 11.

24. A pharmaceutical composition comprising, as an active ingredient, an effective nerve pathology treatment amount of a ganglioside derivative according to claim 13.

25. A pharmaceutical composition comprising, as an active ingredient, an effective nerve pathology treatment amount of a ganglioside derivative according to claim 15.

26. A method for the treatment of pathologies of the nervous system of one affected therewith, comprising administering thereto an effective nerve pathology treatment amount of a ganglioside derivative according to claim 1.

27. A method for the treatment of pathologies of the nervous system of one affected therewith, comprising administering thereto an effective nerve pathology treatment amount of a ganglioside derivative according to claim 2.

28. A method for the treatment of pathologies of the nervous system of one affected therewith, comprising administering thereto an effective nerve pathology treatment amount of a ganglioside derivative according to claim 3.

29. A method for the treatment of pathologies of the nervous system of one affected therewith, comprising administering thereto an effective nerve pathology treatment amount of a ganglioside derivative according to claim 5.

30. A method for the treatment of pathologies of the nervous system of one affected therewith, comprising administering thereto an effective nerve pathology treatment amount of a ganglioside derivative according to claim 7.

31. A method for the treatment of pathologies of the nervous system of one affected therewith, comprising administering thereto an effective nerve pathology treatment amount of a ganglioside derivative according to claim 9.

32. A method for the treatment of pathologies of the nervous system of one affected therewith, comprising administering thereto an effective nerve pathology treatment amount of a ganglioside derivative according to claim 11.

33. A method for the treatment of pathologies of the nervous system of one affected therewith, comprising administering thereto an effective nerve pathology treatment amount of a ganglioside derivative according to claim 13.

34. A method for the treatment of pathologies of the nervous system of one affected therewith, comprising administering thereto an effective nerve pathology treatment amount of a ganglioside derivative according to claim 15.

35. An ester derivative of a ganglioside of the general formula:

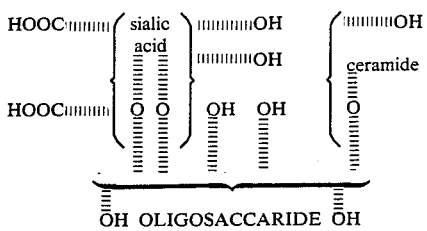

wherein the oligosaccharide moiety is comprised of from 1 to 5 monosaccharides and is connected by a glucosidic bond to a ceramide moiety and to at least one sialic acid moiety, said derivative being an ester derivative in which the carboxyl groups of said sialic acid moieties are esterified with an alcohol, said alcohol being a substituted or unsubstituted alcohol selected from the group consisting of a $C_{1-12}$ aliphatic alcohol, a $C_{1-12}$ araliphatic alcohol with only one benzene ring, a $C_{1-12}$ heterocyclic alcohol with one heterocyclic ring containing a heteroatom selected from the group consisting of N, S and O, a $C_{1-14}$ alicyclic alcohol, and a $C_{1-14}$ aliphaticalicyclic alcohol containing only one cycloaliphatic ring, with the proviso that said ganglioside derivative is not the methyl ester of ganglioside $G_{M1}$ or $G_{M3}$.

36. A ganglioside derivative according to claim 35, wherein the hydroxyl groups of said ceramide moiety and said oligosaccharide moiety are acylated with a carboxylic acid, said carboxylic acid being a substituted or unsubstituted carboxylic acid selected from the group consisting of a $C_{1-10}$ aliphatic, $C_{1-10}$ aromatic, $C_{1-10}$ araliphatic, $C_{1-10}$ alicyclic and $C_{1-10}$ heterocyclic carboxylic acid.

37. A ganglioside derivative comprised of an oligosaccharide moiety formed by 1 to 5 monosaccharides, at least one sialic acid moiety and at least one ceramide moiety, the carboxyl groups of said sialic acid moieties being amidized with an amine, said amine being a substituted or unsubstituted amine selected from the group consisting of ammonia, a $C_{1-12}$ aliphatic amine, a $C_{1-12}$ aromatic amine, a $C_{1-12}$ heterocyclic amine containing a heteroatom selected from the group consisting of N, S and O, a $C_{1-12}$ alicyclic amine, and an araliphatic amine with only one benzene ring and a miximum of 4 carbon atoms in the aliphatic portion.

38. A ganglioside derivative according to claim 37, wherein the hydroxyl groups of said ceramide moiety and said oligosaccharide moiety are acylated with a carboxylic acid, said carboxylic acid being a substituted or unsubstituted carboxylic acid selected from the group consisting of a $C_{1-10}$ aliphatic, $C_{1-10}$ aromatic, $C_{1-10}$ araliphatic, $C_{1-10}$ alicyclic and $C_{1-10}$ heterocyclic carboxylic acid.

39. A ganglioside derivative comprised of an oligosaccharide moiety formed by 1 to 5 monosaccharides, at least one sialic acid moiety and at least one ceramide moiety, the hydroxyl groups in said oligosaccharide, sialic acid and ceramide moieties being acylated with a substituted or unsubstituted carboxylic acid selected from the group consisting of a $C_{1-10}$ aliphatic, $C_{1-10}$ aromatic, $C_{1-10}$ araliphatic, $C_{1-10}$ alicyclic and $C_{1-10}$ heterocyclic carboxylic acid.

* * * * *

UNITED STATES PATENT AND TRADEMARK OFFICE
CERTIFICATE OF CORRECTION

PATENT NO. : 4,713,374

DATED : December 15, 1987

INVENTOR(S) : F. della VAlle et al.

It is certified that error appears in the above-identified patent and that said Letters Patent is hereby corrected as shown below:

Claim 1, last line, after "$G_{M1}$" insert -- , $G_{M2}$, $G_{D1a}$ --.

Claim 11, last line, delete ", $G_{D1a}$".

Claim 12, last line, delete ", $G_{D1a}$".

Claim 35, last line, after "$G_{M1}$" insert -- , $G_{M2}$, $G_{D1a}$ --.

Signed and Sealed this

Seventh Day of June, 1988

Attest:

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,713,374

DATED : December 15, 1987

INVENTOR(S) : Francesco Della Valle and Aurelio Romeo

It is certified that error appears in the above-identified patent and that said Letters Patent is hereby corrected as shown below:

On the title page, Item: "(30) Foreign Application Priority Data" change "June 27, 1984" to read --July 3, 1984--.

Signed and Sealed this

Twenty-ninth Day of March, 1994

Attest:

BRUCE LEHMAN

*Attesting Officer*     *Commissioner of Patents and Trademarks*